United States Patent
Deng et al.

(10) Patent No.: US 10,975,188 B2
(45) Date of Patent: Apr. 13, 2021

(54) RAPID SELF-ASSEMBLED SMALL-SIZED BLOCK POLYMER MATERIAL WITH LOW QUENCHING TEMPERATURE AND THE PREPARATION AND APPLICATION THEREOF

(71) Applicant: FUDAN UNIVERSITY, Shanghai (CN)

(72) Inventors: Hai Deng, Shanghai (CN); Xuemiao Li, Shanghai (CN); Jie Li, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 89 days.

(21) Appl. No.: 15/614,211

(22) Filed: Jun. 5, 2017

(65) Prior Publication Data
US 2018/0208697 A1    Jul. 26, 2018

(30) Foreign Application Priority Data
Jan. 20, 2017    (CN) .......................... 201710048239.X

(51) Int. Cl.
| C08F 293/00 | (2006.01) |
| C07C 69/653 | (2006.01) |
| C08F 297/02 | (2006.01) |

(52) U.S. Cl.
CPC .......... *C08F 293/00* (2013.01); *C07C 69/653* (2013.01); *C08F 297/026* (2013.01)

(58) Field of Classification Search
CPC ..... C08F 257/02; C08F 220/22; C08F 220/24
See application file for complete search history.

(56) References Cited

U.S. PATENT DOCUMENTS

| 6,529,665 B1 * | 3/2003 | Yamashita | ....... B29D 11/00682 |
| | | | 385/124 |
| 2002/0082319 A1 * | 6/2002 | Zhao | ..................... C08F 265/06 |
| | | | 523/201 |

FOREIGN PATENT DOCUMENTS

| CN | 101833253 A | 9/2010 |
| CN | 101899270 A | 12/2010 |
| CN | 103254375 A | 8/2013 |
| CN | 103665726 A | 3/2014 |
| CN | 106750057 A | 5/2017 |
| JP | 2001-206923 | * 1/2000 |

OTHER PUBLICATIONS

Kajiyama et al. Macromolecules 1995, 28, 3482-3484 (Year: 1995).*
Ruiz et al. Journal of Applied Polymer Science vol. 126, 38-45 (Year: 2012).*
Li et al. Macromolecules , 39, 7044-7054 (Year: 2006).*
Zengjiang, Wei; "Preparation and Research of Biotic Super-Hydrophobic Surface"; Shandong Institute of Light Industry, Jinan, China; May 2010.
Zhu Shenmin, Zhang Bin, Li Ming and Yan Deyue; "Synthesis of Poly(styrene-b-methyl methacrylate) block copolymer by ATRP catalyzed by FeCl2/iminodiacetic acid"; China Synthetic Rubber Industry, Jul. 15, 2000, 23(4), 243.

* cited by examiner

*Primary Examiner* — Mark S Kaucher
(74) *Attorney, Agent, or Firm* — Adam Warwick Bess; Matihew Rupert Kaser

(57) ABSTRACT

The present invention relates to a rapid assembled small-sized block polymer material with low quenching temperature and the preparation and application thereof. In particular, the present invention discloses a block copolymer, and glass transition temperature of the block copolymer is less than 120° C. The present invention also discloses the preparation and application of the block copolymer. The block copolymer can achieve excellent phase separation and rapid patterning at a lower annealing temperature (e.g. 80° C.) and a shorter annealing time (e.g. 30 s), and a photolithographic pattern with a very high resolution (e.g. 5 nm half-pitch) can be further obtained by etching, which provides a new photolithographic mean for further extension of Moore's Law to achieve semiconductor photolithography with a resolution of less than 10 nm, or even 5 nm (half-pitch).

8 Claims, 13 Drawing Sheets

RAPID SELF-ASSEMBLED SMALL-SIZED BLOCK POLYMER MATERIAL WITH LOW QUENCHING TEMPERATURE AND THE PREPARATION AND APPLICATION THEREOF

TECHNICAL FIELD

The present invention relates to the field of materials, particularly relates to a rapid assembled small-sized block polymer material with low quenching temperature and the preparation and application thereof.

BACKGROUND ART

The research and development of nanomaterials and nanodevices is a hotspot in the field of materials in the 21st century. It is a common goal pursued by scientific research workers and industrial manufacturers to obtain stable and fine nanostructures quickly and easily. Especially in the field of semiconductor, it is very important to precisely control the size and morphology of the nanostructure so as to obtain microstructure with smaller size defects. This kind of material has a broad application prospect in the next generation of nanoelectronic devices such as semiconductor, display, storage, sensors and drug release. Meanwhile, the nanomaterials also have advantages such as high information storage capacity, rapid working speed, accurate and controllable structure, and portability.

Photolithography technology is one of the most widely used technologies in the micro-graphic processing, and it is also the foundation of the semiconductor industry. However, due to the limitation of light scattering effect and processing technology, it is difficult for current photolithography technology to reach 10 nm scale. It is a simple and efficient method for the preparation of highly ordered nanostructures to use the micro phase separation of the block copolymer.

However, the self-assembly of the existing block copolymer materials (such as PS-b-PMMA) usually requires a higher annealing temperature (above 160° C.) and a longer annealing time (such as 6 hours), and the time-consuming and energy-consuming process is difficult to meet the needs of modern industrial production. In addition, the PS-b-PMMA-based material self-assembled by PS-b-PMMA on the wafer has some defects, which hinders its application in practical production.

To sum up, there is an urgent need in the art to develop a highly-ordered block copolymer material which can achieve rapid self-assembly at low temperature or even at room temperature in a short time and has potential self-healing properties to reduce self-assembly defect rate.

SUMMARY OF THE INVENTION

One object of the present invention is to provide a highly ordered block copolymer material which can achieve rapid self-assembly at low temperature or even at room temperature in a short time, thereby providing a new photolithography mean to get very high resolution.

In the first aspect of the present invention, a block copolymer is provided, glass transition temperature of the block copolymer is less than 120° C.

In another preferred embodiment, the glass transition temperature of the block copolymer is less than 90° C., preferably less than 70° C., more preferably less than 50° C., more preferably less than 40° C., most preferably less than 35° C.

In another preferred embodiment, the block copolymer includes a block A and a block B, wherein the block A is polymerized from a monomer selected from the group consisting of: vinyl and $R_3$ substituted C6-C10 aryl compounds, and vinyl and $R_3$ substituted C6-C10 heteroaryl compounds containing from 0 to 4 heteroatoms selected from N, O, S or P, wherein, $R_3$ is selected from the group consisting of: none, halogen, substituted or unsubstituted C1-C6 alkyl, and substituted or unsubstituted C1-C6 alkoxy; the block B is polymerized from a monomer represented by

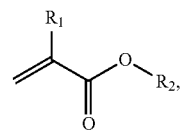

wherein $R_1$ is selected from the group consisting of: H, halogen, substituted or unsubstituted C1-C6 alkyl, substituted or unsubstituted C1-C6 alkoxy, and substituted or unsubstituted C6-C10 aryl, $R_2$ is selected from the group consisting of: substituted or unsubstituted C1-C30 alkyl, and substituted or unsubstituted C3-C30 cycloalkyl; the "substituted" means that the group is substituted with one or more substituents selected from halogen.

In another preferred embodiment, the vinyl and $R_3$ substituted C6-C10 aryl compounds have following structure

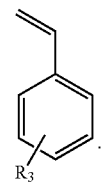

In another preferred embodiment, the vinyl and $R_3$ substituted C6-C10 heteroaryl compounds containing from 0 to 4 heteroatoms selected from N, O, S or P have a structure selected from the group consisting of:

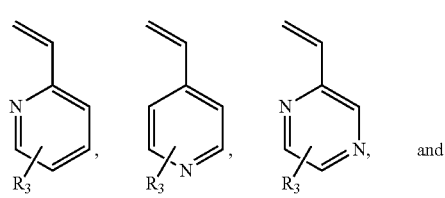

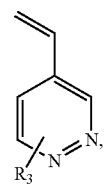

preferably

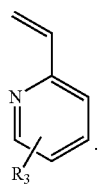

In another preferred embodiment, the halogen is selected from the group consisting of: fluorine, chlorine, bromine, and iodine, preferably fluorine.

In another preferred embodiment, when $R_2$ is substituted C1-C30 alkyl, in $R_2$, the substitution ratio of the substitutents to hydrogen is 10-95%, preferably 25-85%, more preferably 50-80%.

In another preferred embodiment, $R_2$ is substituted C4-C30 alkyl, preferably C6-C30 alkyl, preferably C8-C30 alkyl, preferably C10-C30 alkyl, more preferably C12-C30 alkyl.

In another preferred embodiment, the weight percentage of halogen in the block copolymer is 1-65 wt %, preferably 3-50 wt %, more preferably 5-40 wt %, most preferably 10-30 wt %.

In another preferred embodiment, the molar ratio of the block A to the block B is 1-500:1-500, preferably 3-100:3-100, more preferably 5-60:5-25.

In another preferred embodiment, the mass content of the block A in the block copolymer is 30-90 wt %, preferably 50-70 wt %, more preferably 55-65 wt %.

In another preferred embodiment, the mass content of the block B in the block copolymer is 10-70 wt %, preferably 30-50 wt %, more preferably 35-45 wt %.

In another preferred embodiment, the block copolymer has a structure selected from the group consisting of: A-B diblock structure, A-B-A triblock structure, and B-A-B triblock structure.

In another preferred embodiment, the block A is polymerized from a monomer selected from the group consisting of: styrene, and vinylpyridine; and/or
the block B is polymerized from the monomer represented by

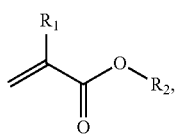

wherein, $R_1$ is selected from the group consisting of: H, and C1-C6 alkyl, $R_2$ is unsubstituted or fluorine-substituted C1-C30 alkyl, in the fluorine-substituted C1-C30 alkyl, the number of the substituent F is 1 to 60.

In another preferred embodiment, in the fluorine-substituted C1-C30 alkyl, the number of the substituent F is 3 to 40, preferably 5 to 25.

In another preferred embodiment, the number of monomers polymerized to form the block A is from 1 to 500, preferably from 3 to 100, more preferably from 5 to 60.

In another preferred embodiment, the number of monomers polymerized to form the block B is from 1 to 500, preferably from 3 to 100, more preferably from 5 to 25.

In another preferred embodiment, the block polymer has one or more characteristics selected from the group consisting of:

1) polydispersity (PDI) of the block copolymer is less than or equal to 1.30, preferably less than or equal to 1.25, more preferably less than or equal to 1.20;

2) number average molecular weight of the block copolymer is from 1000 to 200000, preferably from 5000 to 100000, more preferably from 8000 to 60000;

3) annealing temperature for phase separation and self-assembly of the block copolymer is less than or equal to 200° C., preferably less than or equal to 160° C., more preferably less than or equal to 120° C., more preferably less than or equal to 100° C., most preferably less than or equal to 90° C.;

4) annealing time for phase separation and self-assembly of the block copolymer is less than or equal to 24 h, preferably less than or equal to 5 h, more preferably less than or equal to 1 h, more preferably less than or equal to 15 min, more preferably less than or equal to 5 min, most preferably less than or equal to 1 min;

5) assembly spacing of the product self-assembled by the block copolymer is less than or equal to 100 nm, preferably less than or equal to 50 nm, more preferably less than or equal to 25 nm, more preferably less than or equal to 20 nm, more preferably less than or equal to 15 nm, most preferably less than or equal to 10 nm (i.e. half-pitch is less than or equal to 5 nm).

In another preferred embodiment, the number-average molecular weight of the block copolymer is less than or equal to 20000, preferably less than or equal to 19000, preferably less than or equal to 18000, preferably less than or equal to 17000, preferably less than or equal to 16000, preferably less than or equal to 15000, preferably less than or equal to 14000, preferably less than or equal to 13000, preferably less than or equal to 12000, preferably less than or equal to 11000, more preferably less than or equal to 10000.

In the second aspect of the present invention, a preparation method of the block copolymer in the first aspect of the present invention is provided, and the method comprising the following steps:

1) providing a homopolymer and a modified monomer, wherein,
the homopolymer is polymerized from a monomer selected from the group consisting of: vinyl and $R_3$ substituted C6-C10 aryl compounds, and vinyl and $R_3$ substituted C6-C10 heteroaryl compounds containing from 0 to 4 heteroatoms selected from N, O, S or P, wherein $R_3$ is selected from the group consisting of: none, halogen, substituted or unsubstituted C1-C6 alkyl, substituted or unsubstituted C1-C6 alkoxy;
the modified monomers has a formula of

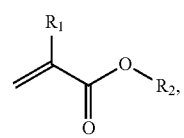

wherein $R_1$ is selected from the group consisting of: H, halogen, substituted or unsubstituted C1-C6 alky, substituted or unsubstituted C1-C6 alkoxy, and substituted or unsubstituted C6-C10 aryl, $R_2$ is selected from the group consisting of: substituted or unsubstituted C1-C30 alkyl, and substituted or unsubstituted C3-C30 cycloalkyl; the "substituted" means that the group is substituted with one or more substituents selected from halogen;

2) mixing the homopolymer and the modified monomer to obtain the block copolymer in the first aspect of the present invention.

In another preferred embodiment, the number average molecular weight of the block copolymer is from 2000 to 10000, preferably from 4000 to 8000, more preferably from 5000 to 7000.

In another preferred embodiment, in step 2), the reaction molar ratio of the homopolymer and the modified monomer is 1-500:1-500, preferably 3-100:3-100, more preferably 5-60:5-25.

In the third aspect of the present invention, a modified monomer is provided, and the modified monomer has a formula of

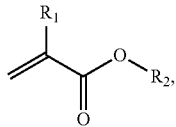

wherein $R_1$ is selected from the group consisting of: H, halogen, substituted or unsubstituted C1-C6 alkyl, substituted or unsubstituted C1-C6 alkoxy, substituted or unsubstituted C6-C10 aryl, $R_2$ is selected from the group consisting of: substituted or unsubstituted C1-C30 alkyl, substituted or unsubstituted C3-C30 cycloalkyl; the "substituted" means that the group is substituted with one or more substituents selected from halogen.

In another preferred embodiment, glass transition temperature of a homopolymer polymerized from the modified monomer is less than or equal to 60° C., preferably less than or equal to 50° C., more preferably less than or equal to 45° C.

In the fourth aspect of the present invention, a composite material is provided, and the composite material comprises the block copolymer in the first aspect of the present invention or is made from the block copolymer in the first aspect of the present invention.

In the fifth aspect of the present invention, a use of the block copolymer in the first aspect of the present invention is provided, wherein the block copolymer is used for the preparation of materials selected from the group consisting of: Directed Self-assembly (DSA) materials, nano-catalyst, functional nano-electronic devices, portable precision storage materials, and biomedical nanodevices.

It should be understood that in the present invention, any of the technical features specifically described above and below (such as in the Examples) can be combined with each other, thereby constituting new or preferred technical solutions which will not redundantly be described one by one herein.

DETAILED DESCRIPTION OF THE INVENTION

Figure 1:
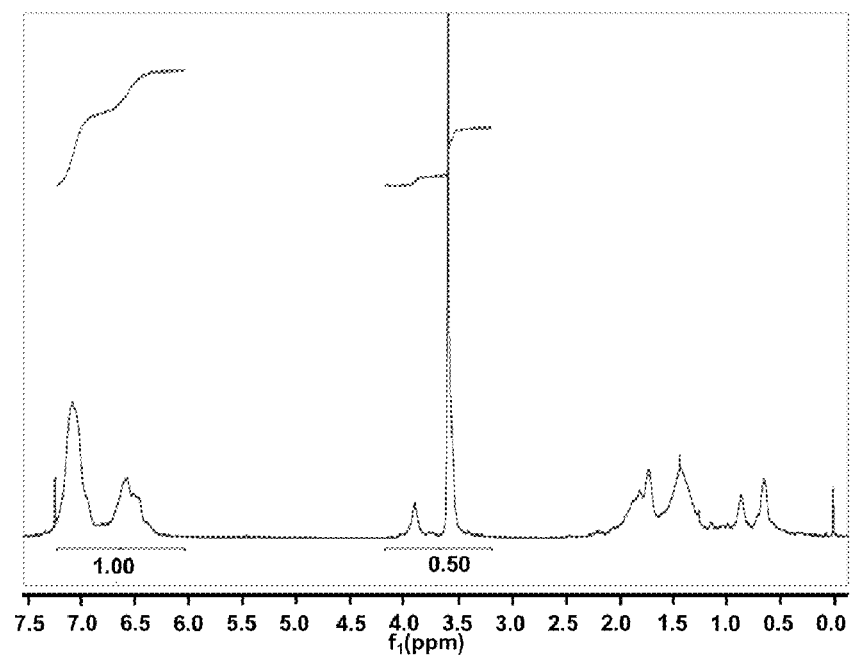
FIG. 1 is a $^1$H-NMR spectrum of the block copolymer PS-PPDFMA-3-21.

Through extensive and intensive long research, the inventors have prepared a modified PS-PMMA-type block polymer material, and the block polymer material can achieve excellent phase separation and rapid self-assembly at lower annealing temperature (such as 80° C.) in shorter annealing time (such as 30 s), and the product obtained by self-assembly has very low defect rate and extremely small size (such as full-pitch is less than or equal to 10 nm, and half-pitch is less than or equal to 5 nm), thus significantly promoting the application of nanoelectronic devices. On this basis, the inventors have completed the present invention.

Terms

In the present invention, terms "modified PS-PMMA-type low Tg polymer material", "modified PS-PMMA-type low Tg block polymer material", "modified polymer material", "low Tg polymer material", "block polymer material" or "block copolymers" are exchangeable.

Block Copolymer

Glass transition temperature (Tg) refers to frontier issues of polymer dynamics and thermodynamics. Specifically, glass transition is inherent nature of amorphous polymer materials and it is a macroreflection of the transition of polymer chains movement, which directly affects the performance and processing properties of the materials. According to different movement forms of the polymer, the majority of polymer materials are usually in the following four kinds of physical state (or mechanical state): glass state, viscoelastic state, high elastic state (rubber state) and viscous flow state. And the glass transition is a transition between high elastic state and glass state, from the molecular structure, the glass transition temperature is a relaxation phenomenon of the amorphous portion of the polymer from the frozen state to the thawed state. When the temperature is below Tg, the polymer is in glass state and both the molecular chains and the segments can not move, and only atoms (or groups) constituting the molecule can vibrate at their equilibrium positions. However, at the glass transition temperature, the molecular chains still can not move, but the chain segments start to move, which exhibits high elastic properties. When the temperature increases again, the whole molecular chains start to move, which exhibits viscous flow properties.

Based on this, the present invention provides a block copolymer, and the glass transition temperature of the block copolymer is less than 120° C.

In another preferred embodiment, the glass transition temperature of the block copolymer is less than 90° C., preferably less than 70° C., more preferably less than 50° C., more preferably less than 40° C., most preferably less than 35° C.

Typically, the block copolymer includes a block A and a block B, wherein the block A is polymerized from a monomer selected from the group consisting of: vinyl and $R_3$ substituted C6-C10 aryl compounds, and vinyl and $R_3$ substituted C6-C10 heteroaryl compounds containing from 0 to 4 heteroatoms selected from N, O, S or P, wherein $R_3$ is selected from the group consisting of: none, halogen, substituted or unsubstituted C1-C6 alkyl, and substituted or unsubstituted C1-C6 alkoxy; the block B is polymerized from a monomer represented by:

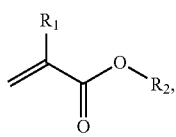

wherein $R_1$ is selected from the group consisting of: H, halogen, substituted or unsubstituted C1-C6 alkyl, substituted or unsubstituted C1-C6 alkoxy, and substituted or unsubstituted C6-C10 aryl, $R_2$ is selected from the group consisting of: substituted or unsubstituted C1-C30 alkyl, and substituted or unsubstituted C3-C30 cycloalkyl; the "substituted" means that the group is substituted with one or more substituents selected from halogen.

In another preferred embodiment, the vinyl and $R_3$ substituted C6-C10 aryl compounds have following structure:

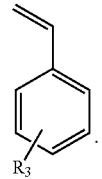

In another preferred embodiment, the vinyl and $R_3$ substituted C6-C10 heteroaryl compounds containing from 0 to 4 heteroatoms selected from N, O, S or P have a structure selected from the group consisting of:

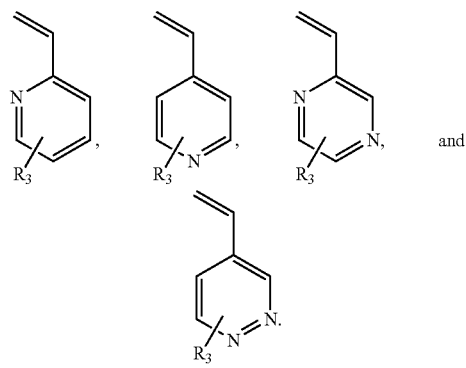

In another preferred embodiment, the halogen is selected from the group consisting of: fluorine, chlorine, bromine, and iodine.

In another preferred embodiment, when $R_2$ is substituted C1-C30 alkyl, in $R_2$, the substitution ratio of the substitutents to hydrogen is 10-95%, preferably 25-85%, more preferably 50-80%.

In another preferred embodiment, the weight percentage of halogen in the block copolymer is 1-65 wt %, preferably 3-50 wt %, more preferably 5-40 wt %, most preferably 10-30 wt %.

In the present invention, the molar ratio of the block A to the block B is 1-500:1-500, preferably 3-100:3-100, more preferably 5-60:5-25.

In another preferred embodiment, the mass content of the block A in the block copolymer is 30-90 wt %, preferably 50-70 wt %, more preferably 55-65 wt %.

In another preferred embodiment, the mass content of the block B in the block copolymer is 10-70 wt %, preferably 30-50 wt %, more preferably 35-45 wt %.

In the present invention, the block copolymer has a structure that includes, but is not limited to, the following groups: A-B diblock structure, A-B-A triblock structure and B-A-B triblock structure.

Preferably, the block A is polymerized from a monomer selected from the group consisting of: styrene, and vinylpyridine; and/or the block B is polymerized from a monomer represented by

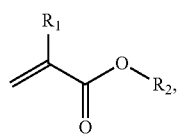

wherein, $R_1$ is selected from the group consisting of: H, and C1-C6 alkyl, $R_2$ is unsubstituted or fluorine-substituted C1-C30 alkyl, in the fluorine-substituted C1-C30 alkyl, the number of the substituent F is 1 to 60.

In another preferred embodiment, in the fluorine-substituted C1-C30 alkyl, the number of the substituent F is 3 to 40, preferably 5 to 25.

In another preferred embodiment, the number of monomers polymerized to form the block A is from 1 to 500, preferably from 3 to 100, more preferably from 5 to 60.

In another preferred embodiment, the number of monomers polymerized to form the block B is from 1 to 500, preferably from 3 to 100, more preferably from 5 to 25.

Preferably, the block polymer has one or more characteristic selected from the group consisting of:

1) polydispersity (PDI) of the block copolymer is less than or equal to 1.30, preferably less than or equal to 1.25, more preferably less than or equal to 1.20.

2) number average molecular weight of the block copolymer is from 1000 to 200000, preferably from 5000 to 100000, more preferably from 8000 to 60000;

3) annealing temperature for phase separation and self-assembly of the block copolymer is less than or equal to 200° C., preferably less than or equal to 160° C., more preferably less than or equal to 120° C., more preferably less than or equal to 100° C., most preferably less than or equal to 90° C.;

4) annealing time for phase separation and self-assembly of the block copolymer is less than or equal to 24 h, preferably less than or equal to 5 h, more preferably less than or equal to 1 h, more preferably less than or equal to 15 min, more preferably less than or equal to 5 min, most preferably less than or equal to 1 min;

5) assembly spacing of the product self-assembled by the block copolymer is less than or equal to 100 nm, preferably less than or equal to 50 nm, more preferably less than or equal to 25 nm, more preferably less than or equal to 20 nm, more preferably less than or equal to 15 nm, most preferably less than or equal to 10 nm (i.e. half-pitch is less than or equal to 5 nm).

It should be understood that the block copolymer in the present invention has lower glass transition temperature, and one of the blocks exhibits high elastic state at room temperature, so it can self-assemble into a highly ordered structure by thermal annealing for a short time (e.g. 30 s) at low temperature (e.g. 80° C.) or even room temperature without heating.

Furthermore, the block copolymer in the present invention has a certain self-healing properties at room temperature, and one block can move freely in the assembled structure, thus making the edge of the assembled structure smoother to a certain extent and greatly reducing defects of the assembled structure.

In addition, the present invention also provides a modified monomer, and the modified monomer has a formula of

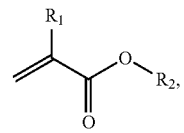

wherein $R_1$ is selected from the group consisting of: H, halogen, substituted or unsubstituted C1-C6 alkyl, substituted or unsubstituted C1-C6 alkoxy, and substituted or unsubstituted C6-C10 aryl, $R_2$ is selected from the group consisting of: substituted or unsubstituted C1-C30 alkyl, and substituted or unsubstituted C3-C30 cycloalkyl; the "substituted" means that the group is substituted with one or more substituents selected from halogen.

In another preferred embodiment, glass transition temperature of a homopolymer polymerized from the modified monomer is less than or equal to 60° C., preferably less than or equal to 50° C., more preferably less than or equal to 45° C.

Additionally, it should be understood that

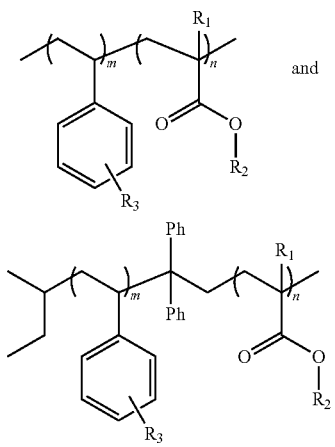

and have same meaning, so they can be used interchangeably in the present invention. For example,

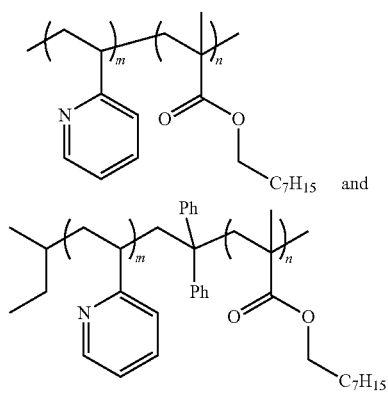

have same meaning, and they can be used interchangeably. It should be understood that structure

on the left of above molecule is a end group of sec-butyl lithium after initiating the reaction, and 1,1-diphenylethylene between the two blocks acts as a stabilizer for anion, and these structures have no impact on the phase separation and self-assembly of the block polymer.

It should be understood that, in the block B of the block copolymer of the present invention, the length of carbon chains of $R_2$ and the property of substituent group therein have great influence on the performance of the block copolymers. Specifically, with the increasing length of carbon chains of $R_2$, the assembly spacing of the block copolymer after annealing decreases, thereby a photolithographic pattern with a very high resolution (e.g. full-pitch is less than or equal to 15 nm, preferably less than or equal to 12 nm, preferably less than or equal to 10 nm, more preferably less than or equal to 8 nm) can be further obtained by etching.

Additionally, it should also be understood that, in the block copolymer of the present invention, the structure of the block A also has great influence on the performance of the block copolymer. Specifically, compared with the block polymer wherein the monomer of the block A is the vinyl and $R_3$ substituted C6-C10 aryl compounds

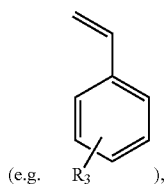

(e.g. $R_3$), the block polymer wherein the monomer of the block A is vinyl and $R_3$ substituted C6-C10 heteroaryl compounds containing from 0 to 4 heteroatoms selected from N, O, S or P (e.g.

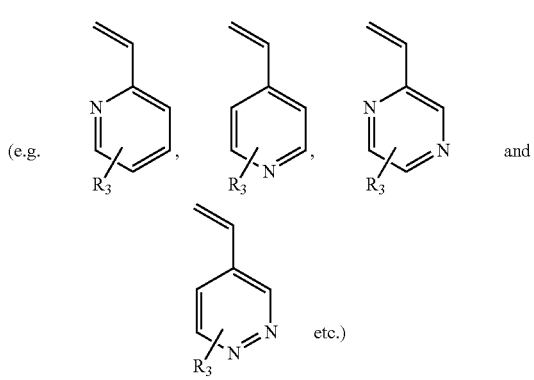

(e.g. $R_3$ , $R_3$ , $R_3$ and $R_3$ etc.)

has better phase separation properties, and the assembly spacing thereof is smaller, and a photolithographic pattern with a very high resolution (e.g. full-pitch is less than or equal to 15 nm, preferably less than or equal to 12 nm, preferably less than or equal to 10 nm, more preferably less than or equal to 8 nm) can be further obtained by etching.

Preparation Method

The present invention also provides a preparation method of the block copolymer, and the method comprising the following steps:

1) providing a homopolymer and a modified monomer, wherein, the homopolymer is polymerized from a monomer selected from the group consisting of: vinyl and $R_3$ substituted C6-C10 aryl compounds, and vinyl and $R_3$ substituted C6-C10 heteroaryl compounds containing from 0 to 4 heteroatoms selected from N, O, S or P, wherein $R_3$ is selected from the group consisting of: none, halogen, substituted or unsubstituted C1-C6 alkyl, and substituted or unsubstituted C1-C6 alkoxy;

the modified monomers has a formula of

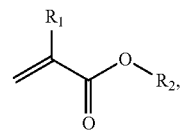

wherein $R_1$ is selected from the group consisting of: H, halogen, substituted or unsubstituted C1-C6 alkyl, substituted or unsubstituted C1-C6 alkoxy, and substituted or unsubstituted C6-C10 aryl, $R_2$ is selected from the group consisting of: substituted or unsubstituted C1-C30 alkyl, and substituted or unsubstituted C3-C30 cycloalkyl; the "substituted" means that the group is substituted with one or more substituents selected from halogen;

2) mixing the homopolymer and the modified monomer to obtain the block copolymer.

In another preferred embodiment, the number average molecular weight of the block copolymer is from 2000 to 10000, preferably from 4000 to 8000, more preferably from 5000 to 7000.

In another preferred embodiment, in step 2), the reaction molar ratio of the homopolymer and the modified monomer is 1-500:1-500, preferably 3-100:3-100, more preferably 5-60:5-25.

Application

The present invention also provides a composite material, and the composite material comprises the block copolymer or is made from the block copolymer.

The present invention also provides a use of the block copolymer, which the block copolymer is used for the preparation of materials selected from the group consisting of: Directed Self-assembly (DSA) materials, nano-catalyst, functional nano-electronic devices, portable precision storage materials, and biomedical nanodevices.

Compared with the prior art, the present invention has following main advantages:

(1) the modified PS-PMMA-type rapid assembled polymer material with low quenching temperature can achieve excellent phase separation and rapid patterning at a lower annealing temperature (e.g. 80° C.) and a shorter annealing time (e.g. 30 s);

(2) the modified PS-PMMA-type block polymer material can achieve a certain degree of microphase separation at room temperature;

(3) the modified PS-PMMA-type block polymer material has a certain self-healing properties, and one block can move freely at room temperature, thus greatly reducing defects of the assembled structure, which lay a good foundation for post-selective etching and applications;

(4) the modified PS-PMMA-type rapid assembled block polymer material with low quenching temperature can be used to construct lamella structure or the hexagonal phase structure by adjusting the ratio of two blocks;

(5) the preparation method of the modified PS-PMMA-type rapid assembled block polymer material with low quenching temperature has following advantages: simple, safe and low cost, and a block copolymer having smaller PDI can be prepared;

(6) photolithography with a photoresist containing the block copolymer can obtain a resolution of half-pitch<5 nm.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Unless otherwise defined, all professional and scientific terminology used in the text have the same meanings as known to the skilled in the art. In addition, any methods and materials similar or equal with the record content can apply to the methods of the invention. The method of the preferred embodiment described herein and the material are only for demonstration purposes.

Pre-Treatment of Raw Materials

The tetrahydrofuran (THF) and cyclohexane were firstly dried with $CaH_2$ overnight, followed by atmospheric distillation, and the obtained were treated with $MgBu_2$ (1M in hexane) before the reaction and then transferred to the reaction flask. Styrene and the modified methacrylate monomers with low quenching temperature were firstly washed twice with 5% NaOH, and then sequentially washed with $H_2O$ and saturated brine and dried with $MgSO_4$. The obtained was dried with $CaH_2$ overnight, and then treated with triisobutylaluminum before the reaction, and then transferred to the reaction flask.

The synthetic steps are shown below (Take anionic polymerization as an example)

Step one:

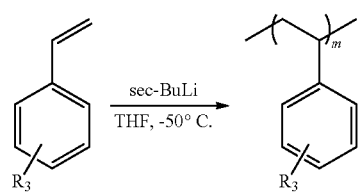

Step two:

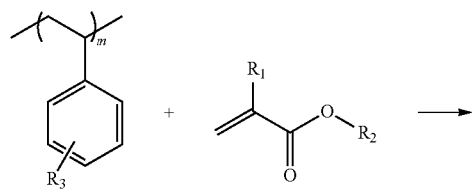

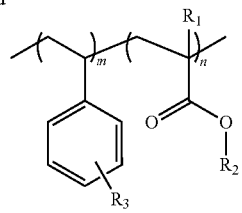

General Testing Methods:

$^1$H-NMR

400 MHz Fourier Transform Nuclear Magnetic Resonance Spectrometer (AVANCE III) was used in this invention to determine the specific structure of the materials, and deuterated chloroform was used as solvent. The structure, components ratio and polymer molecular weight of the material were determined by peak integration of the characteristic peak position of the hydrogen atom in the structural formula.

GPC

In the present invention, the number average molecular weight and polydispersity (PDI) were measured by gel chromatography (THF phase), and then corrected using a universal calibration method, and styrene was used as calibration reference.

SAXS

The small angle x-ray scattering (SAXS) was used in the present invention to measure the assembled structure and size of the polymer material, and the assembled size and microstructure thereof were calculated according to the peak positions and proportions of the highest peak and the secondary peak. The tested samples were polymer powder or thin film after quenching at a low temperature.

DSC

The Differential Scanning Calorimetry (Q2000) was used in the present invention to measure the glass transition temperature (Tg) of the material. The temperature procedure was to raise the temperature by 20° C./min from −60° C. to 160° C., and then the temperature was lowered to −60° C. by same rate, as the first cycle, and the main object thereof was to eliminate the thermal history of the samples, and the second cycle raising temperature procedure is still to raise the temperature by 20° C./min from −60° C. to 160° C.

TEM

The transmission electron microscope (Tecnai $G^2$20 twin) was used in the present invention to measure the specific appearance of the microstructure of the material, and the tested samples were polymer powder or thin films after quenching at a low temperature. The dark area of the image represents the block A with a high electron density in the material, while the light area thereof represents the block B with a small electron density in the material. The assembled structure and size obtained by TEM image were corresponding to those obtained by SAXS image (full pitch was less than or equal to 10 nm and half pitch was less than or equal to 5 nm), and both were corresponding to the diffraction pattern, which show a long-range ordered assembled structure.

The illustration on low quenching temperature and time: the block polymer was formulated into a solution, and then dropped on a silicon wafer, after the solvent evaporated to dryness, and then the wafer was placed onto a pre-heated hot plate (the temperature of the hot plate is between 60° C. to 150° C., preferably 80° C. or 100° C.), after a certain period of time (such as 10 s to 500 s, preferably 30 s, 1 min, 5 min, 1 h), the wafer was placed onto the ice and quenched rapidly. The assembled polymer powder or thin film was then scraped off to test SAXS and TEM.

Example 1 the Preparation of Class a Block Copolymer PS-PPDFMA-3-21 ($R_1$=$CH_3$, $R_2$=$C_{12}H_{10}F_{15}$, $R_3$=None)

3 ml styrene

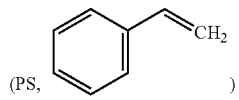

and 30 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −40° C. for 15 min. 0.5 ml sec-BuLi (1M in hexane) was added, and kept at −40° C. and reacted for 15 min. The temperature of the dried modified methacrylate monomer A quenched at low temperature (1.6 g) was reduced to −30° C., and then the obtained was dropped into the reaction system containing styrene, keeping at −40° C. and reacted for 30 min. The product was precipitated in ethanol to give 3.5 g of white solid.

FIG. 1 is a $^1$H-NMR spectrum of the block copolymer PS-PPDFMA-3-21.

It can be seen from FIG. 1 that the characteristic H peaks of the PS block and the PPDFMA block are corresponding to the structures indicated above, and their integral area are also consistent with the feed ratio of above two kinds of monomers.

The GPC analysis shows that the number average molecular weight of the block copolymer PS-PPDFMA-3-21 is 16800 and PDI thereof is 1.13.

Figure 15:
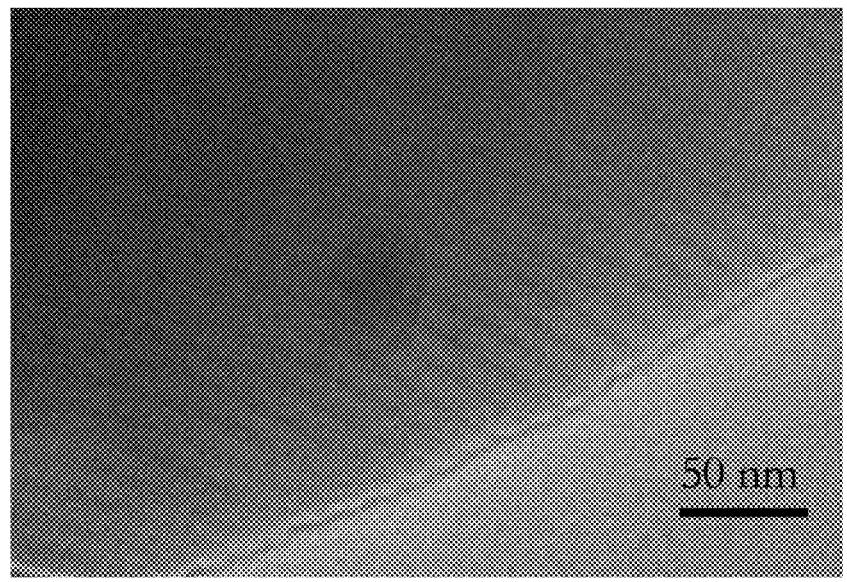
FIG. 15 is a TEM diagram of the block copolymer PS-PPDFMA-3-21.

FIG. 15 is a TEM diagram of the block copolymer PS-PPDFMA-3-21.

It can be seen from FIG. 15 that, in the Figure, the lines with different tone respectively represent the distribution of the two kinds of assembled components in the microstructure, and the interphase distribution of the dark area and the light area forms the lamella structure, and the sum of the two areas is "full-pitch" mentioned above. As shown in FIG. 15, there are four or so repeating units in the 50 nm coordinate scale, and the size of the repeating unit (i.e. full-pitch) is about 13.8 nm by calculation, which means a stripe with 7 nm resolution can be obtained after selectively etching of one single component. Furthermore, in SAXS diagram, the lamella spacing of PS-PPDFMA-3-21 is calculated to be 14.9 nm, which is consistent with the TEM results.

Figure 16:
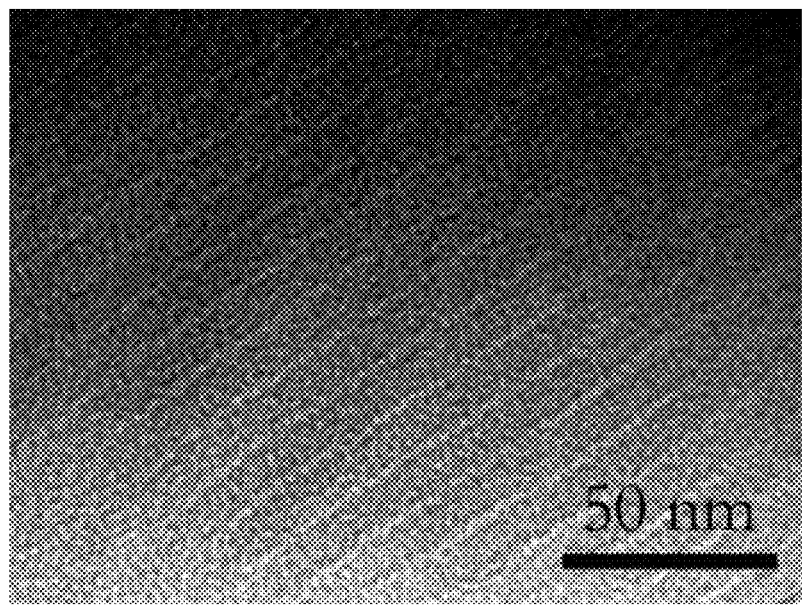
FIG. 16 is also a TEM diagram of the block copolymer PS-PPDFMA-3-21.

FIG. 16 is also a TEM diagram of the block copolymer PS-PPDFMA-3-21, and the size and the structure thereof correspond to FIG. 15.

Figure 17:
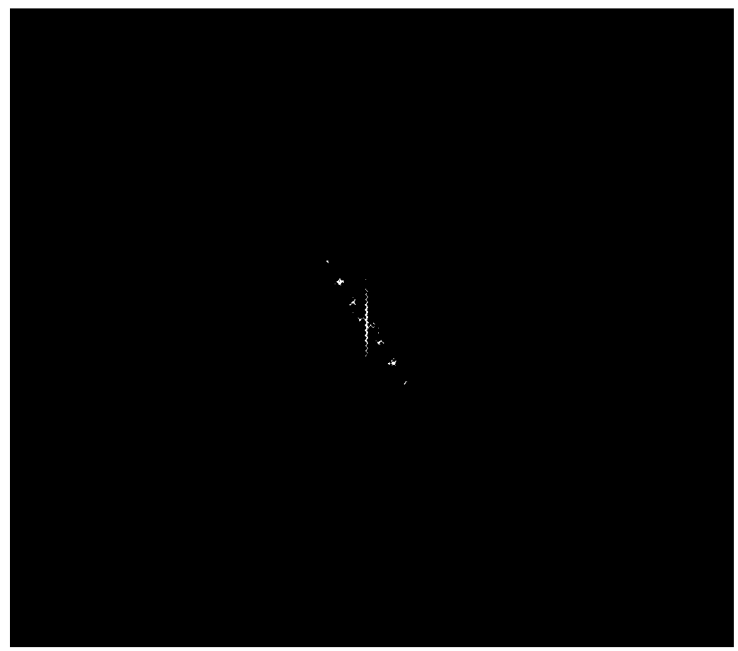
FIG. 17 is a TEM diffraction pattern of the designated area in FIG. 16.

FIG. 17 is a TEM diffraction pattern of the designated area in FIG. 16, which shows that it is arranged in long-range order in one direction.

Example 2 the Reparation of Class a Block Copolymer PS-PPDFMA-3-46 ($R_1$=$CH_3$, $R_2$=$C_{12}H_{10}F_{15}$, $R_3$=None)

2 ml styrene and 30 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (1M in hexane) was added and kept at −50° C. and reacted for 15 min. The temperature of the dried modified methacrylate monomer A (1.6 g) was reduced to −30° C., and then the obtained was dropped into the reaction system containing styrene, keeping at −50° C. and reacted for 30 min. The product was precipitated in ethanol to give 2.6 g of white solid in 90% yield.

The $^1$H-NMR spectrum of the block copolymer PS-PPDFMA-3-46 is similar to FIG. 1.

The GPC results of the block copolymer PS-PPDFMA-3-46 are similar to those of PS-PPDFMA-3-21, and the number average molecular weight thereof is 12500 and PDI thereof is 1.10.

Figure 18:
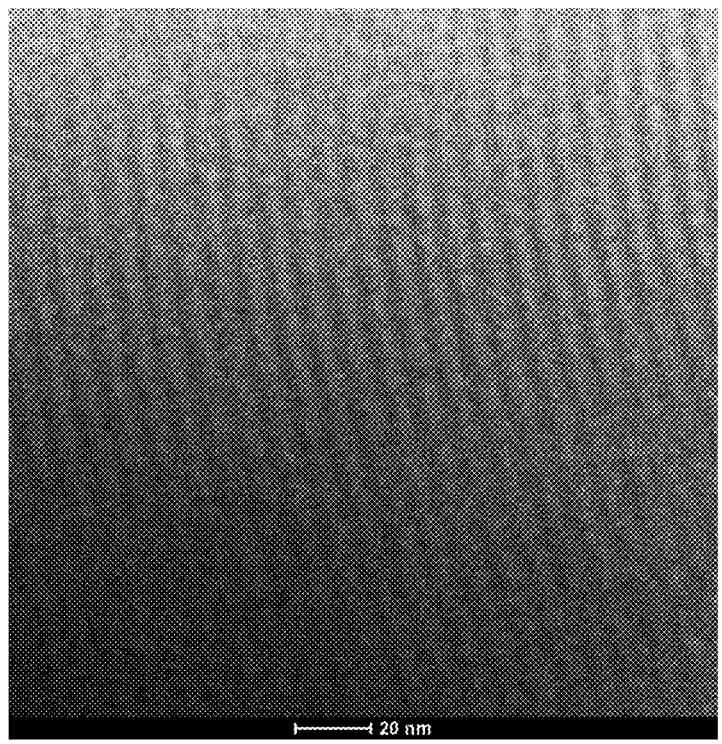
FIG. 18 and FIG. 19 are TEM diagrams of the block copolymer PS-PPDFMA-3-46.
Figure 19:
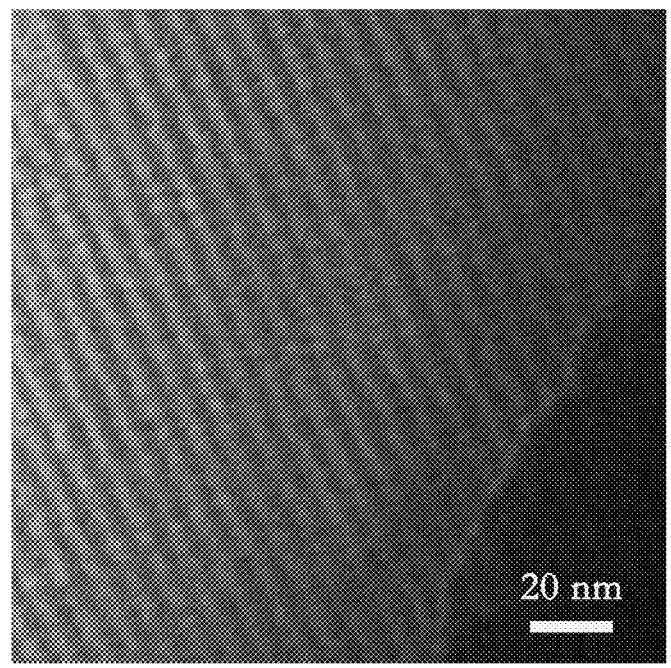

FIG. 18 and FIG. 19 are TEM diagrams of the block copolymer PS-PPDFMA-3-46.

It can be seen from FIG. 18 that there are three or so repeating units in the 20 nm coordinate scale, and the size of the repeating unit (i.e. full-pitch) is about 8.6 nm by calculation, which means a stripe with 4 nm resolution can be obtained after selectively etching of one single component. Furthermore, in SAXS diagram, the lamella spacing of PS-PPDFMA-3-46 is calculated to be 10.3 nm, which is consistent with the TEM results.

The contents described in FIG. 19 are basically same as those of FIG. 18.

Example 3 the Preparation of Class a Block Copolymer PS-PPDFMA-3-47 ($R_1$=$CH_3$, $R_2$=$C_{12}H_{10}F_{15}$, $R_3$=None)

1.5 ml styrene and 30 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (1M in hexane) was added and the solution rapidly became orange-red, keeping at −50° C. and reacted for 15 min. The temperature of the dried modified methacrylate monomer A (1.6 g) was reduced to −30° C., and then the obtained was dropped into the reaction system containing styrene, keeping at −50° C. and reacted for 30 min. The product was precipitated in ethanol to give 2.2 g of white solid.

The $^1$H-NMR spectrum of the block copolymer PS-PPDFMA-3-47 is similar to FIG. 1.

The GPC analysis shows the number average molecular weight of the block copolymer PS-PPDFMA-3-47 is 11300 and PDI thereof is 1.09.

Figure 5:
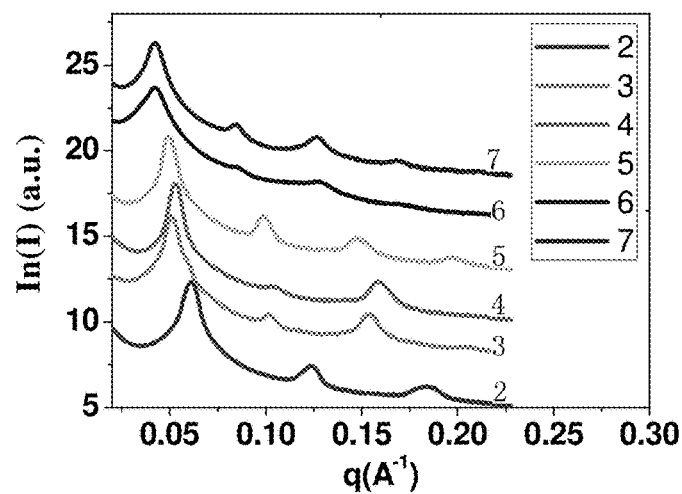
FIG. 5 is a SAXS diagram of the self-assembled product of the block copolymer PS-PPDFMA (samples 2-7) after thermal quenching at a low temperature (e.g., 80° C.) for a short time (e.g., 60 s).

FIG. 5 is a SAXS diagram of the self-assembled product of the block copolymer PS-PPDFMA (samples 2-7) after thermal quenching at a low temperature (e.g., 80° C.) for a short time (e.g., 60 s).

Specifically, the parameters of the samples in FIG. 5 are shown in Table 1 below:

TABLE 1

| Example | Sample | m:n | Assembly lamella spacing(full-pitch) |
|---|---|---|---|
| 3 | 1 | 0.8 | 8.7 nm |
| 2 | 2 | 1.7 | 10.3 nm |
|  | 3 | 2.6 | 11.8 nm |
|  | 4 | 2.7 | 12.3 nm |
|  | 5 | 3.3 | 12.8 nm |
|  | 6 | 4.1 | 14.8 nm |

TABLE 1-continued

| Example | Sample | m:n | Assembly lamella spacing(full-pitch) |
|---|---|---|---|
| 1 | 7 | 4.3 | 14.9 nm |
|   | 10 | 6.5 | 15.7 nm |

The samples 3, 4, 5, 6 and 10 were prepared in the same manner as in Example 1, and the difference is that the amount of styrene used is 2.3 ml, 2.5 ml, 2.6 ml, 2.9 ml and 3.5 ml, respectively.

The illustration of SAXS diagram is as follows: based on the abscissa q value corresponding to the highest peak in the left (i.e. the first scattered peak), the assembly spacing (i.e. d value, i.e. full-pitch) can be obtained by using the formula $d=2\pi/q$; and the multi-level peaks behind can be used to determine the morphology of the assembled structure, if the ratio is 1:2:3:4 . . . , then the assembled structure is lamella structure; if the ratio is $1:\sqrt{3}:2:\sqrt{7}$ . . . , then the assembled structure is hexagonal phase structure.

In combination with FIG. 5, it can be seen that, after quenching at low temperature for a short time, Samples 2-7 all have a long-range ordered lamella structure, and the peak type is sharp, and the secondary peaks are obvious. The corresponding full-pitch can be calculated from the abscissa corresponding to the peak position of the highest peak, which indicates that Class A block polymer material can be quickly assembled at low temperature and different sizes thereof can be obtained according to different molecular weight and composition ratio.

Figure 6:
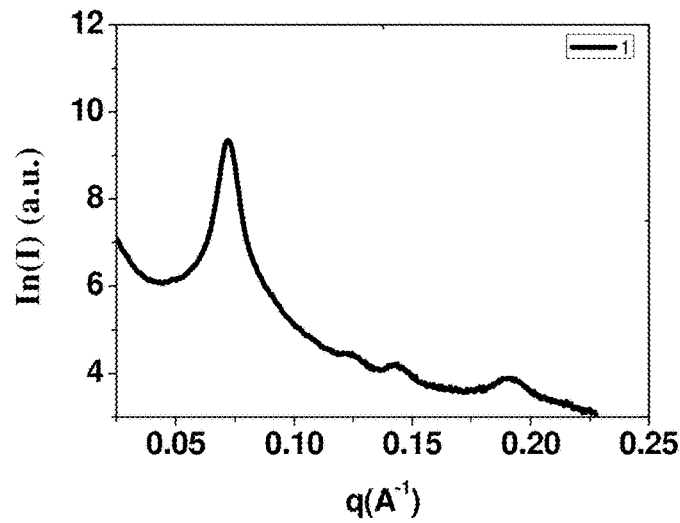
FIG. 6 is a SAXS diagram of the self-assembled product of the Class A block copolymer PS-PPDFMA (sample 1) after thermal quenching at a low temperature (e.g., 80° C.) for a short time (e.g., 60 s).

FIG. 6 is a SAXS diagram of the self-assembled product of the Class A block copolymer PS-PPDFMA (sample 1) after thermal quenching at a low temperature (e.g., 80° C.) for a short time (e.g., 60 s).

Figure 7:
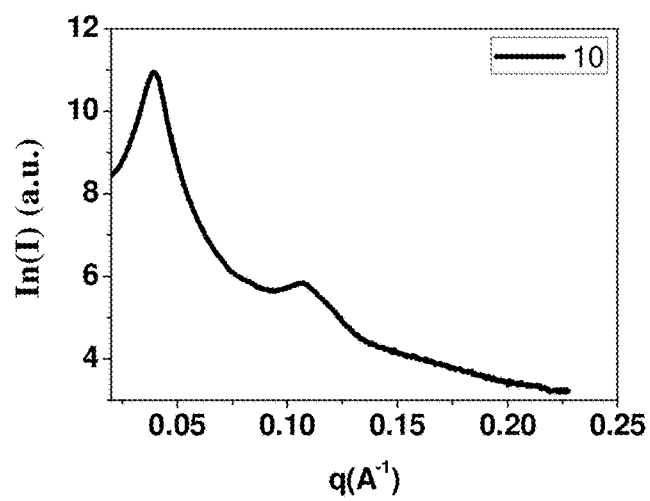
FIG. 7 is a SAXS diagram of the self-assembled product of the Class A block copolymer PS-PPDFMA (sample 10) after thermal quenching at a low temperature (e.g., 80° C.) for a short time (e.g., 60 s).

FIG. 7 is a SAXS diagram of the self-assembled product of the Class A block copolymer PS-PPDFMA (sample 10) after thermal quenching at a low temperature (e.g., 80° C.) for a short time (e.g., 60 s).

It can be seen from FIG. 6 in combination with FIG. 7 that sample 1 and sample 10 have hexagonal phase columnar structure.

Figure 20:
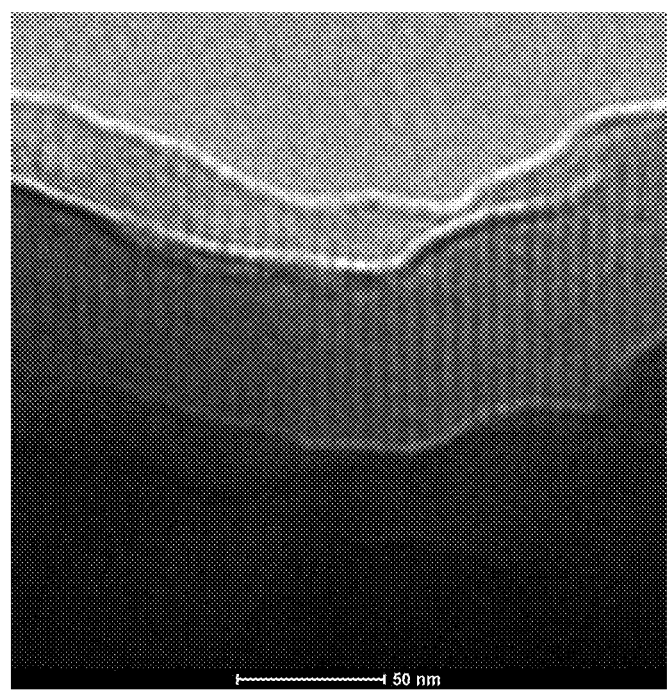
FIG. 20 is a TEM diagram of the block copolymer PS-PPDFMA-3-47.

FIG. 20 is a TEM diagram of the block copolymer PS-PPDFMA-3-47.

It can be seen from FIG. 20 that there are eight or so repeating units in the 50 nm coordinate scale, and the size of the repeating unit (i.e. full-pitch) is about 6.5 nm by calculation, which means a stripe with about 3 nm resolution can be obtained after selectively etching of one single component. Furthermore, in SAXS diagram, the lamella spacing of PS-PPDFMA-3-47 is calculated to be 8.7 nm, which is consistent with the TEM results.

Figure 11:
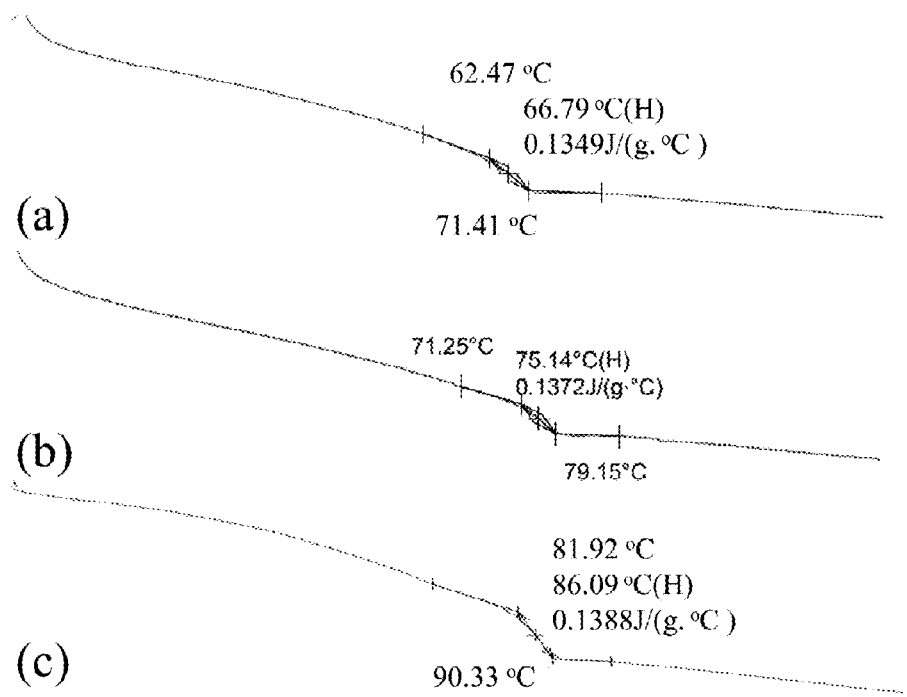
FIG. 11 is a DSC chart of the Class A block copolymer PS-PPDFMA, (a) PS-PPDFMA-3-47, (b) PS-PPDFMA-3-46, (c) PS-PPDFMA-3-21.

FIG. 11 is a DSC chart of the Class A block copolymer PS-PPDFMA, (a) PS-PPDFMA-3-47, (b) PS-PPDFMA-3-46, (c) PS-PPDFMA-3-21.

It can be seen from FIG. 11 that the Tg of the Class A block copolymers PS-PPDFMA are 66° C., 75° C. and 86° C., respectively.

Compared with traditional PS-PMMA block copolymer materials having a Tg of 100° C. to 110° C., the chain movement of above materials need lower energy and temperature, which contributes to the rapid self-assembly thereof at relatively low temperature.

In addition, in order to facilitate the analysis and discussion, homocopolymer PPDFMA polymerized from methacrylate monomer A ($R_1$=H, $R_2$=$C_{12}H_{10}F_{15}$) was further prepared, and the specific preparation process was as follows:

The purified methacrylate monomer A was dissolved in re-evaporated acetonitrile solvent, 1/100 mole eq of AIBN was added as initiator, and the reaction system was heated to 65° C. and stirred for 12 h. The product was then precipitated in ethanol to give the homocopolymer.

Figure 12:
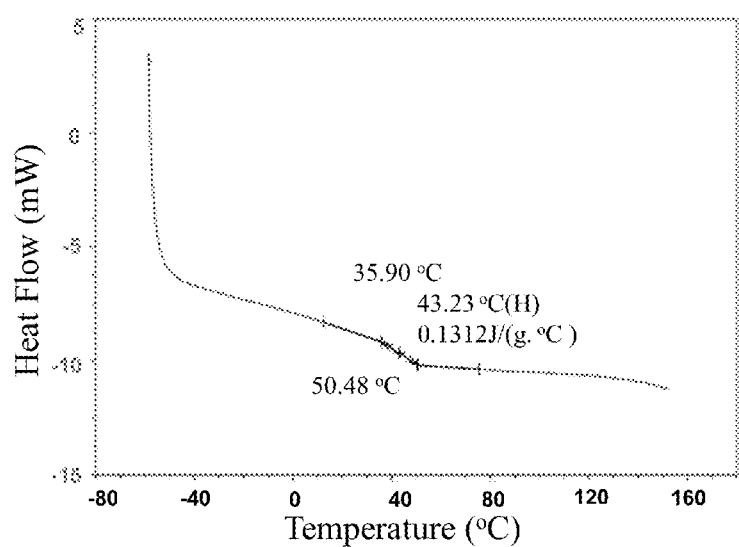
FIG. 12 is a DSC chart of the homopolymer PPDFMA.

FIG. 12 is a DSC chart of the homopolymer PPDFMA.

It can be seen from FIG. 12 that the Tg of the homopolymer PPDFMA is about 43° C., which indicates that the above modified block is a vital factor for the block polymer material of the present invention to be rapid self-assembled at low quenching temperature.

Example 4 the Preparation of Class B Block Copolymer PS-PFMBA-0831 ($R_1$=$CH_3$, $R_2$=$C_4H_2F_7$, $R_3$=None)

2.5 ml styrene and 30 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (1M in hexane) was added and the solution rapidly became orange-red, keeping at −50° C. and reacted for 15 min. The temperature of the dried modified methacrylate monomer B (2 ml) with low quenching temperature was reduced to −30° C., and then the obtained was dropped into the reaction system containing styrene, keeping at −50° C. and reacted for 30 min. The product was precipitated in ethanol to give 4 g of white solid.

Figure 2:
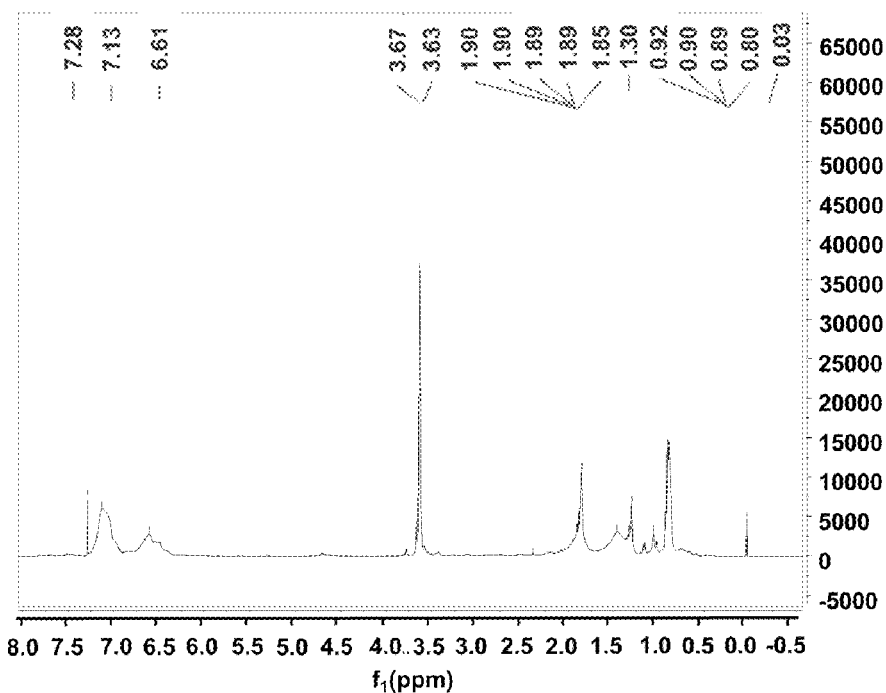
FIG. 2 is a $^1$H-NMR spectrum of the block copolymer PS-PFMBA-0831.

FIG. 2 is a $^1$H-NMR spectrum of the block copolymer PS-PFMBA-0831.

It can be seen from FIG. 2 that the characteristic H peaks of the PS block and the PFMBA block are corresponding to the structures indicated above, and their integral area are also consistent with the feed ratio of above two kinds of monomers.

The GPC analysis shows that the number average molecular weight of the block copolymer PS-PFMBA-0831 is 12500 and PDI thereof is 1.15.

Figure 8:
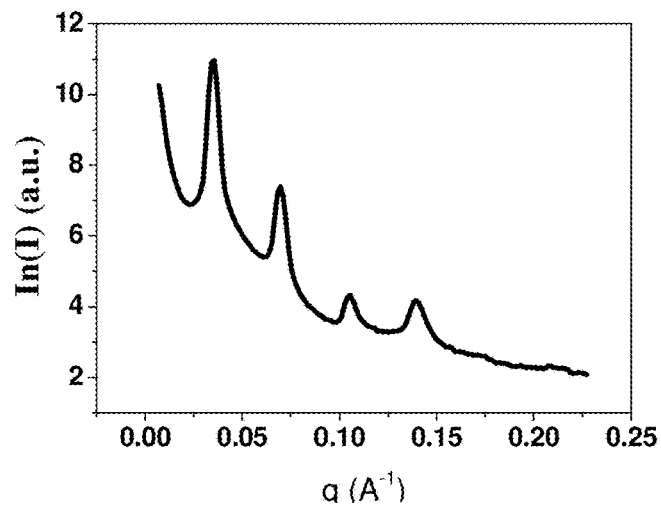
FIG. 8 is a SAXS diagram of the self-assembled product of the Class B block copolymer PS-PFMBA-0831 after thermal quenching at a low temperature (e.g., 80° C.) for a short time (e.g., 60 s).

FIG. 8 is a SAXS diagram of the self-assembled product of the Class B block copolymer PS-PFMBA-0831 after thermal quenching at a low temperature (e.g., 80° C.) for a short time (e.g., 60 s).

Example 5 the Preparation of Class B Block Copolymer PS-PFMBA-0824 ($R_1$=$CH_3$, $R_2$=$C_4H_2F_7$, $R_3$=None)

2 ml styrene and 30 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −50° C. for 15 min. 0.4 ml sec-BuLi (1M in hexane) was added, and kept at −50° C. and reacted for 15 min. The temperature of the dried methacrylate monomer B with low quenching temperature (2 ml) was reduced to −30° C., and then the obtained was dropped into the reaction system containing styrene, keeping at −50° C. and reacted for 30 min. The product was precipitated in ethanol to give 3.6 g of white solid.

The 1H-NMR spectrum of the block copolymer PS-PFMBA-0824 is similar to FIG. 2.

The GPC analysis shows that the number average molecular weight of the block copolymer PS-PFMBA-0824 is 16200 and PDI thereof is 1.13.

Figure 9:
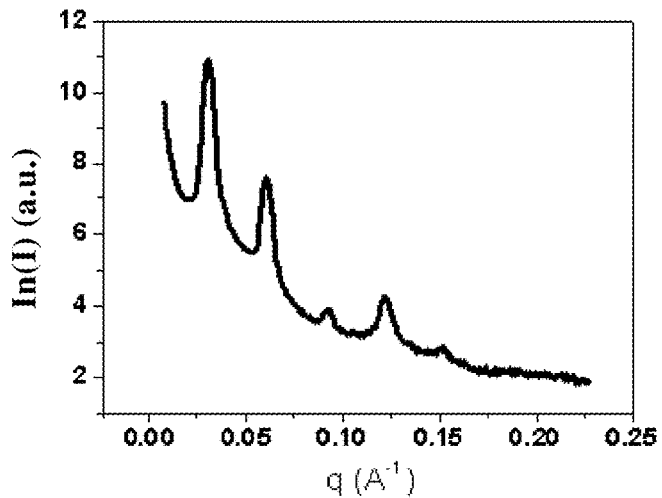
FIG. 9 is a SAXS diagram of the self-assembled product of the Class B block copolymer PS-PFMBA-0824 after thermal quenching at a low temperature (e.g., 80° C.) for a short time (e.g., 60 s).

FIG. 9 is a SAXS diagram of the self-assembled product of the Class B block copolymer PS-PFMBA-0824 after thermal quenching at a low temperature (e.g., 80° C.) for a short time (e.g., 60 s).

It can be seen from FIG. 8 in combination with FIG. 9 that the assembled structures of PS-PFMBA-0831 and PS-PFMBA-0824 are lamella morphology, and the full-pitch thereof are 17.7 nm and 21.0 nm respectively.

Figure 21:
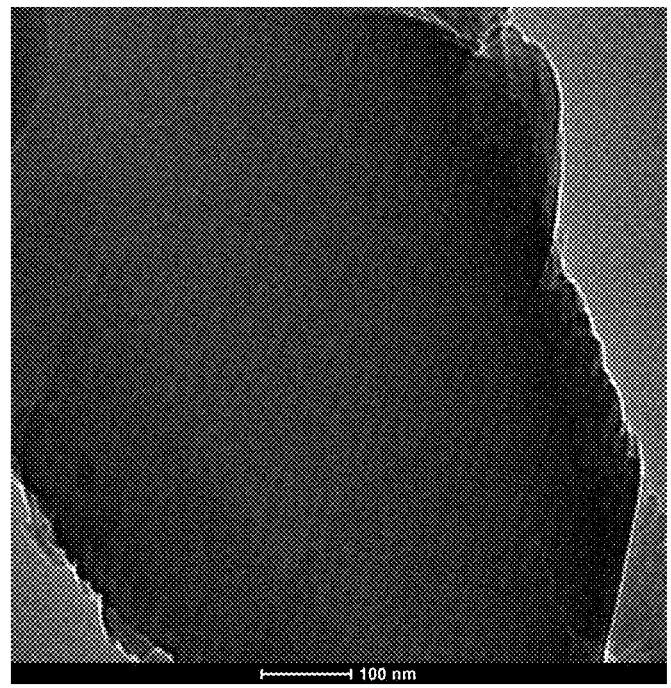
FIG. 21 is a TEM diagram of the block copolymer PS-PFMBA-0824.

FIG. 21 is a TEM diagram of the block copolymer PS-PFMBA-0824. The size thereof is about 20.3 nm by calculation, which is consistent with the SAXS results.

Example 6 the Preparation of Class B Block Copolymer PS-PFMBA-0821 ($R_1$=$CH_3$, $R_2$=$C_4H_2F_7$, $R_3$=None)

3 ml styrene and 30 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −30° C. for 15 min. 0.5 ml sec-BuLi (1M in hexane) was added and kept at −50° C. and reacted for 15 min. The temperature of the dried methacrylate monomer B with low quenching temperature (2.6 ml) was reduced to −50° C., and then the obtained was dropped into the reaction system containing styrene, keeping at −50° C. and reacted for 30 min. The product was precipitated in ethanol to give 4.8 g of white solid.

The $^1$H-NMR spectrum of the block copolymer PS-PFMBA-0821 is similar to FIG. 2.

The GPC analysis shows that the number average molecular weight of the block copolymer PS-PFMBA-0821 is 19600 and PDI thereof is 1.14.

Figure 13:
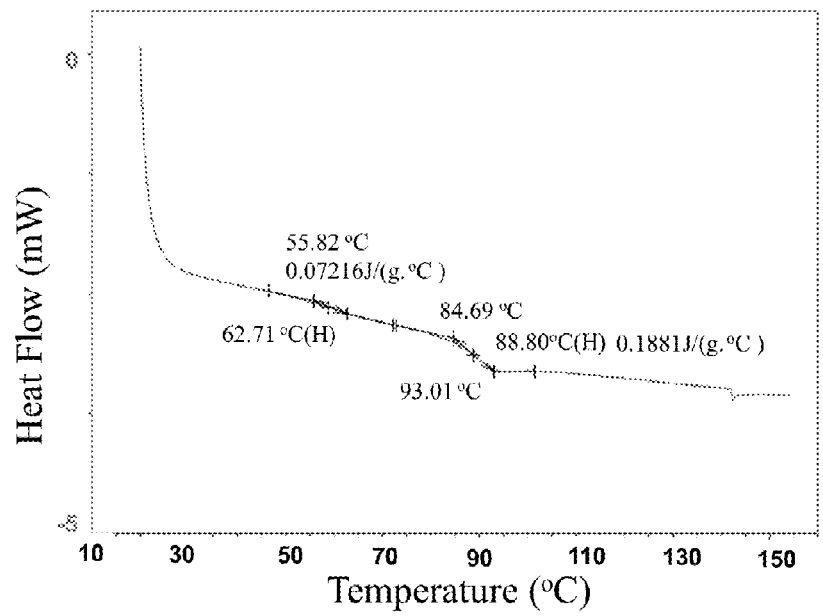
FIG. 13 is a DSC chart of the Class B block copolymer PS-PFMBA-0821.

FIG. 13 is a DSC chart of the Class B block copolymer PS-PFMBA-0821.

It can be seen from FIG. 13 that the Tg of the Class B block copolymer PS-PFMBA-0821 is 58° C. and 88° C., which contributes to the rapid self-assembly of above block polymer after quenching at low temperature.

Example 7 the Preparation of Class C Block Copolymer PS-PFMAA-3-58 ($R_1$=$CH_3$, $R_2$=$C_{10}H_9F_{12}$, $R_3$=None)

2 ml styrene and 30 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (1M in hexane) was added and kept at −50° C. and reacted for 15 min. The temperature of the dried modified methacrylate monomer C (2 ml) was reduced to −30° C., and then the obtained was dropped into the reaction system containing styrene, keeping at −50° C. and reacted for 30 min. The product was precipitated in ethanol to give 2.8 g of white solid.

Figure 3:
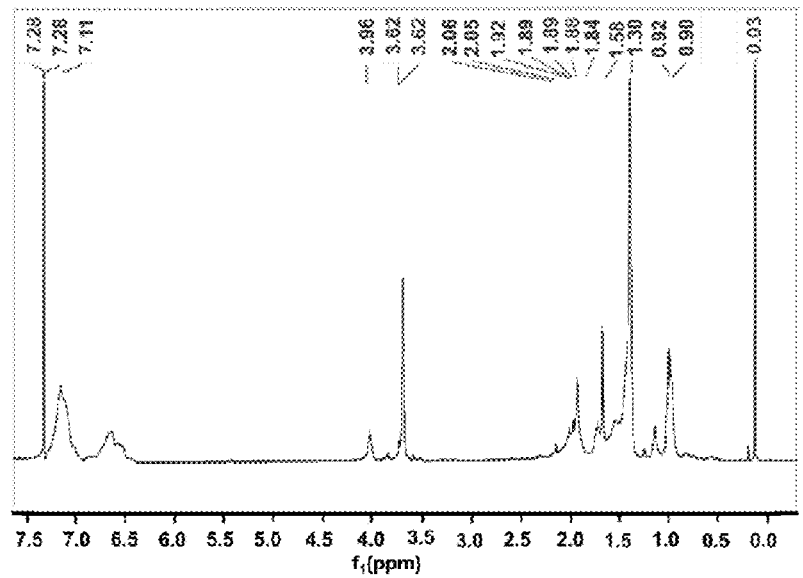
FIG. 3 is a $^1$H-NMR spectrum of the block copolymer PS-PFMAA-3-58.

FIG. 3 is a $^1$H-NMR spectrum of the block copolymer PS-PFMAA-3-58.

It can be seen from FIG. 3 that the characteristic H peaks of the PS block and the PFMAA block are corresponding to the structures indicated above, and their integral area are also consistent with the feed ratio of above two kinds of monomers.

The GPC analysis shows that the number average molecular weight of the block copolymer PS-PFMAA-3-58 is 11400 and PDI thereof is 1.17.

Figure 10:
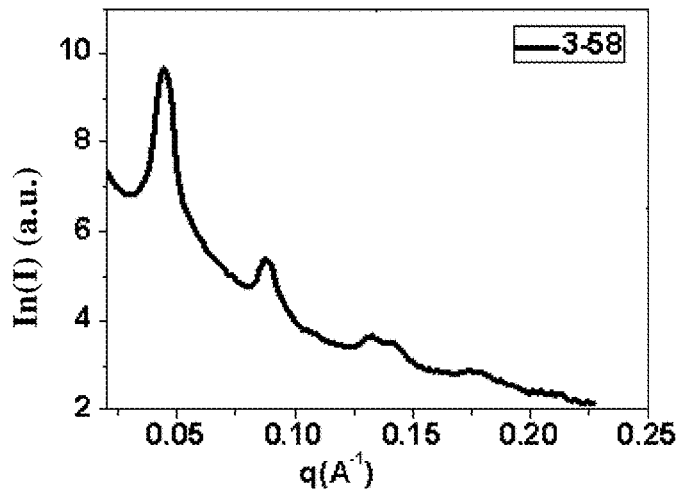
FIG. 10 is a SAXS diagram of the self-assembled product of the Class C block copolymer PS-PFMAA-3-58 after thermal quenching at a low temperature (e.g., 80° C.) for a short time (e.g., 60 s).

FIG. 10 is a SAXS diagram of the self-assembled product of the Class C block copolymer PS-PFMAA-3-58 after thermal quenching at a low temperature (e.g., 80° C.) for a short time (e.g., 60 s). It can be seen from FIG. 10 that it can be rapid assembled at low temperature to obtain a long-range ordered lamella structure.

Figure 22:
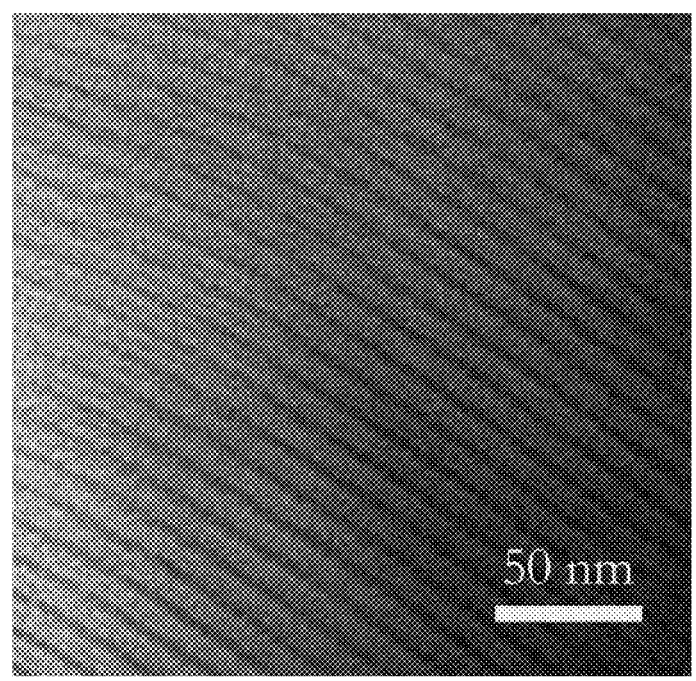
FIG. 22 is a TEM diagram of the block copolymer PS-PFMAA-3-58.

FIG. 22 is a TEM diagram of the block copolymer PS-PFMAA-3-58, and the size (i.e. full-pitch) thereof is about 11.5 nm by calculation, which is consistent with the SAXS results.

Example 8 the Preparation of Class D Block Copolymer PS-PDLMA-1101 ($R_1$=$CH_3$, $R_2$=$C_{10}H_{21}$, $R_3$=None)

2.5 ml styrene and 30 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −50° C. for 15 min. 0.4 ml sec-BuLi (1M in hexane) was added and the solution rapidly became orange-red, and kept at −50° C. and reacted for 15 min. The temperature of 2.5 ml dried modified methacrylate monomer D was reduced to −30° C., and then the obtained was dropped into the reaction system containing styrene, keeping at −50° C. and reacted for 30 min. The product was precipitated in ethanol to give 3.6 g of white solid.

Figure 4:
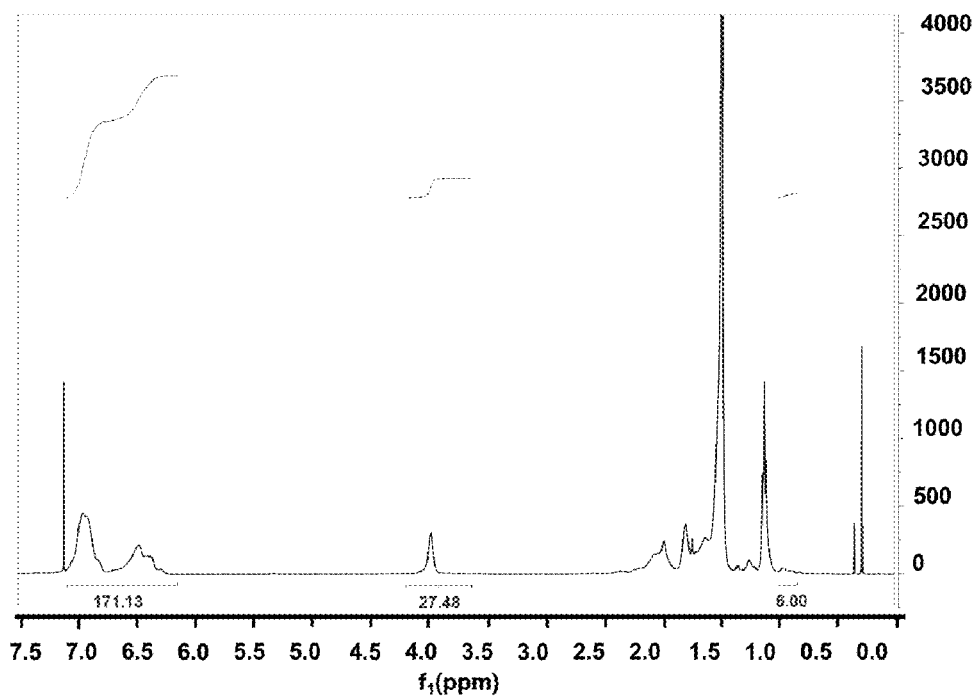
FIG. 4 is a $^1$H-NMR spectrum of the block copolymer PS-PDLMA-1101.

FIG. 4 is a $^1$H-NMR spectrum of the block copolymer PS-PDLMA-1101.

It can be seen from FIG. 4 that the characteristic H peaks of the PS block and the PDLMA block are corresponding to the structures indicated above, and their integral area are also consistent with the feed ratio of above two kinds of monomers.

The GPC analysis shows that the number average molecular weight of the block copolymer PS-PDLMA-1101 is 18300 and PDI thereof is 1.19.

Figure 14:
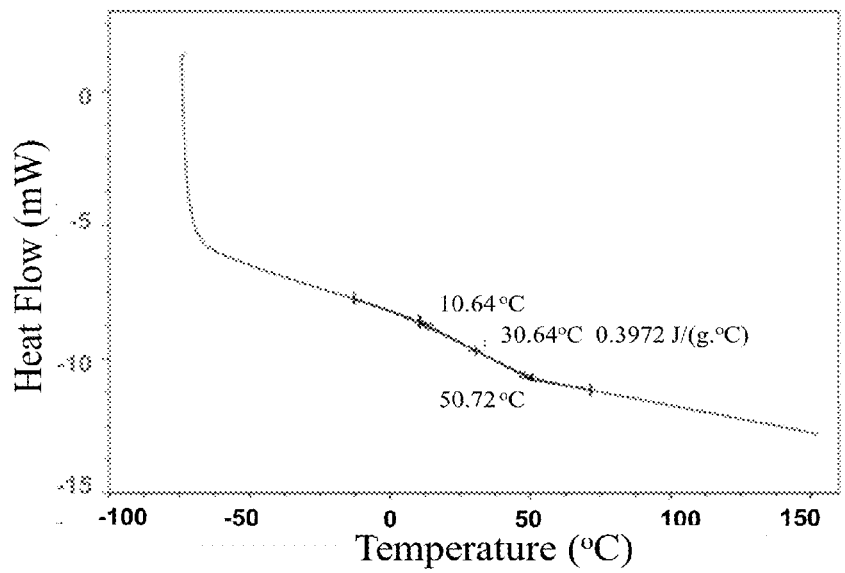
FIG. 14 is a DSC chart of the Class C block copolymer PS-PDLMA-1101.

FIG. 14 is a DSC chart of the Class C block copolymer PS-PDLMA-1101.

It can be seen from FIG. 14 that the Tg of PS-PDLMA-1101 is 30° C., which contributes to the rapid assembly thereof at lower quenching temperature.

Example 9 the Preparation of Class D Block Copolymer PS-PDLMA-1103 ($R_1$=$CH_3$, $R_2$=$C_{10}H_{21}$, $R_3$=None)

2.5 ml styrene and 30 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −50° C. for 15 min. 0.4 ml sec-BuLi (1M in hexane) was added and the solution rapidly became orange-red, kept at −50° C. and reacted for 15 min. The temperature of 2 ml dried modified methacrylate monomer D was reduced to −30° C., and then the obtained was dropped into the reaction system containing styrene, keeping at −50° C. and reacted for 30 min. The product was precipitated in ethanol to give 3.3 g of white solid.

The $^1$H-NMR spectrum of the block copolymer PS-PDLMA-1103 is similar to FIG. 4.

The GPC analysis shows that the number average molecular weight of the block copolymer PS-PDLMA-1103 is 14400 and PDI thereof is 1.16.

Example 9' the Preparation of Class D Block Copolymer PS-PDLMA-1103' ($R_1$=H, $R_2$=$C_{10}H_{21}$, $R_3$=None)

Same as Example 9, and the difference is that the modified methacrylate monomer D is replaced with the modified methacrylate monomer D'.

The performance of the block copolymer obtained in Example 9'($R_1$=H) is the same as that in Example 9($R_1$=$CH_3$), and the performance of the block copolymer obtained in Example 9($R_1$=$CH_3$) is better.

Example 10 the Preparation of Class E Block Copolymer PS-PPFMA-1 ($R_1$=$CH_3$, $R_2$=$C_8H_2F_{15}$, $R_3$=None)

2.5 ml styrene and 25 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (1M in hexane) was added and kept at −50° C. and reacted for 15 min. The temperature of the dried modified methacrylate monomer E (1.8 g) was reduced to −30° C., and then the obtained was dropped into the reaction system containing styrene, keeping at −50° C. and reacted for 30 min. The product was precipitated in ethanol to give 3.3 g of white solid in 90% yield.

The GPC analysis shows that the number average molecular weight of the block copolymer PS-PPFMA-1 is 5500 and PDI thereof is 1.14.

According to the SAXS diagram of the self-assembled product of the Class E block copolymer PS-PPFMA-1 after thermal quenching at a low temperature (e.g., 80° C.) for a short time (e.g., 60 s), the assembly-spacing(full-pitch) of the block copolymer PS-PPFMA-1 is 12.5 nm.

Example 11 the Preparation of Class E Block Copolymer PS-PPFMA-2 ($R_1$=$CH_3$, $R_2$=$C_8H_2F_{15}$, $R_3$=None)

2 ml styrene and 25 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (1M in hexane) was added and kept at −50° C. and reacted for 15 min. The temperature of the dried modified methacrylate monomer E (1.8 g) was reduced to −30° C., and then the obtained was dropped into the reaction system containing styrene, keeping at −50° C. and reacted for 30 min. The product was precipitated in ethanol to give 3.0 g of white solid in 90% yield.

The GPC analysis shows that the number average molecular weight of the block copolymer PS-PPFMA-2 is 3900 and PDI thereof is 1.14.

According to the SAXS diagram of the self-assembled product of the Class E block copolymer PS-PPFMA-2 after thermal quenching at a low temperature (e.g., 80° C.) for a short time (e.g., 60 s), the assembly-spacing of the block copolymer PS-PPFMA-2(full-pitch) is 10.4 nm.

Example 12 the Preparation of Class E Block Copolymer PS-PPFMA-3 ($R_1$=$CH_3$, $R_2$=$C_8H_2F_{15}$, $R_3$=None)

1.6 ml styrene and 25 ml THF were treated with $MgBu_2$ solution (1M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (1M in hexane) was added and kept at −50° C. and reacted for 15 min. The temperature of the dried modified methacrylate monomer E (1.8 g) was reduced to −30° C., and then the obtained was dropped into the reaction system containing styrene, keeping at −50° C. and reacted for 30 min. The product was precipitated in ethanol to give 2.5 g of white solid in 90% yield.

The GPC analysis shows that the number average molecular weight of the block copolymer PS-PPFMA-3 is 3500 and PDI thereof is 1.13.

According to the SAXS diagram of the self-assembled product of the Class E block copolymer PS-PPFMA-3 after thermal quenching at a low temperature (e.g., 80° C.) for a short time (e.g., 60 s), the assembly-spacing(full-pitch) of the block copolymer PS-PPFMA-3 is 8.8 nm.

Example 13 the Preparation of Class F Block Copolymer P2VP-PPFMA-3-57 ($R_1$=$CH_3$, $R_2$=$C_8H_2F_{15}$, $R_3$=None)

3 ml 2-vinylpyridine and 35 ml THF were treated with triisobutylaluminum solution (1M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (1M in hexane) was added and the solution rapidly became orange-red, keeping at −50° C. and reacted for 15 min. The temperature of the dried modified methacrylate monomer F (2.2 ml) was reduced to −30° C., and then the obtained was dropped into the reaction system containing 2-vinylpyridine, keeping at −50° C. and reacted for 30 min. The product was precipitated in ethanol to give 4.3 g of white solid.

Figure 23:
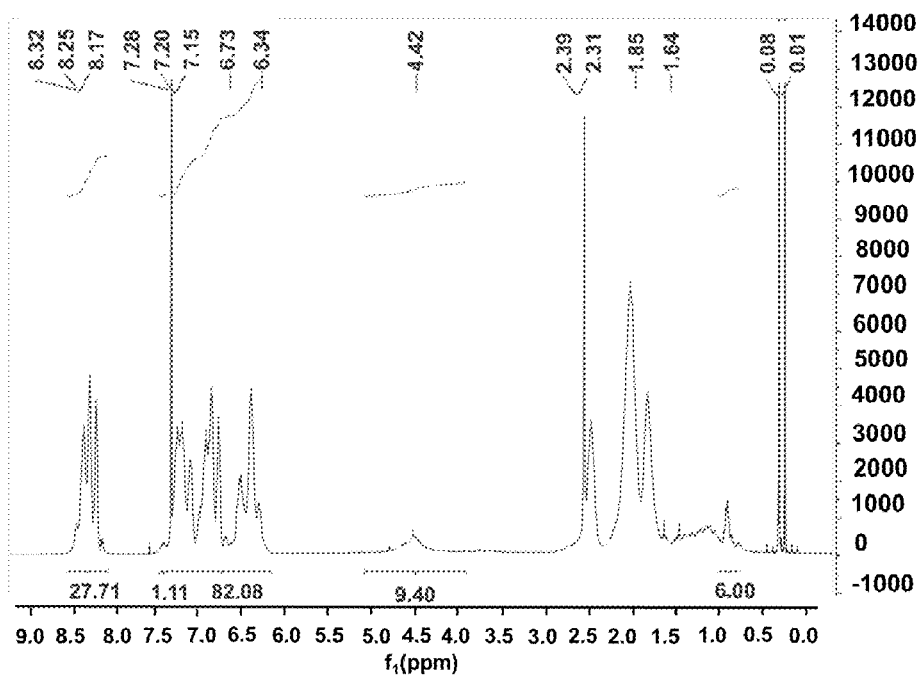
FIG. 23 is a $^1$H-NMR spectrum of the block copolymer P2VP-PPFMA-3-57.

FIG. 23 is a $^1$H-NMR spectrum of the block copolymer P2VP-PPFMA-3-57.

It can be seen from FIG. 23 that the characteristic H peaks of the P2VP block and the PPFMA block are corresponding to the structures indicated above, and their integral area are also consistent with the feed ratio of above two kinds of monomers.

The GPC analysis shows that the number average molecular weight of the block copolymer P2VP-PPFMA-3-57 is 7800 and PDI thereof is 1.14.

Figure 24:
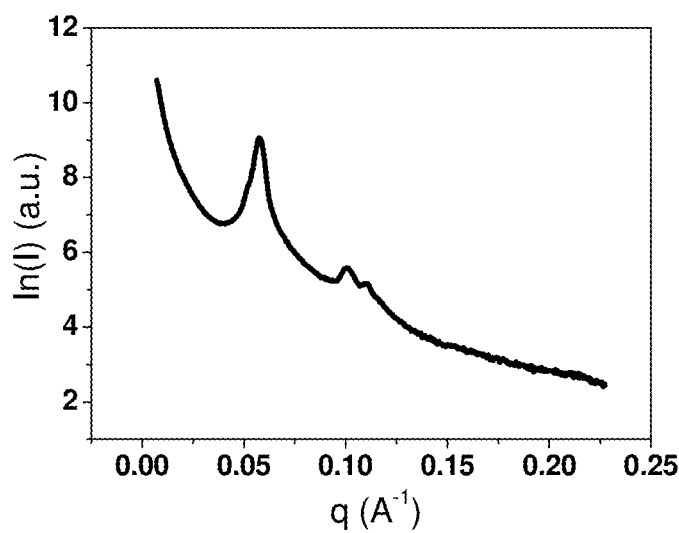
FIG. 24 is a SAXS diagram of the self-assembled product of the Class E block copolymer P2VP-PPFMA-3-57 after thermal quenching at a low temperature (e.g., 160° C.) for a short time (e.g., 60 s).

FIG. 24 is a SAXS diagram of the self-assembled product of the Class E block copolymer P2VP-PPFMA-3-57 after thermal quenching at a low temperature (e.g., 160° C.) for a short time (e.g., 60 s).

It can be seen from FIG. 24 that the block copolymer P2VP-PPFMA-3-57 can be rapid assembled at low temperature to obtain a long-range ordered hexagonal structure, and the assembly-spacing of the block copolymer P2VP-PPFMA-3-57(full-pitch) is 10.9 nm.

Example 14 the Preparation of Class F Block Copolymer P2VP-PPFMA-3-67 ($R_1$=$CH_3$, $R_2$=$C_8H_2F_{15}$, $R_3$=None)

1.5 ml 2-vinylpyridine and 35 ml THF were treated with triisobutylaluminum solution (1M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (1M in hexane) was added and the solution rapidly became orange-red, keeping at −50° C. and reacted for 15 min. The temperature of the dried modified methacrylate monomer F (1.6 ml) was reduced to −30° C., and then the obtained was dropped into the reaction system containing 2-vinylpyridine, keeping at −50° C. and reacted for 30 min. The product was precipitated in ethanol to give 2.6 g of white solid.

The $^1$H-NMR spectrum of the block copolymer P2VP-PPFMA-3-67 is similar to FIG. 23.

The GPC analysis shows that the number average molecular weight of the block copolymer P2VP-PPFMA-3-67 is 8200 and PDI thereof is 1.15.

Figure 25:
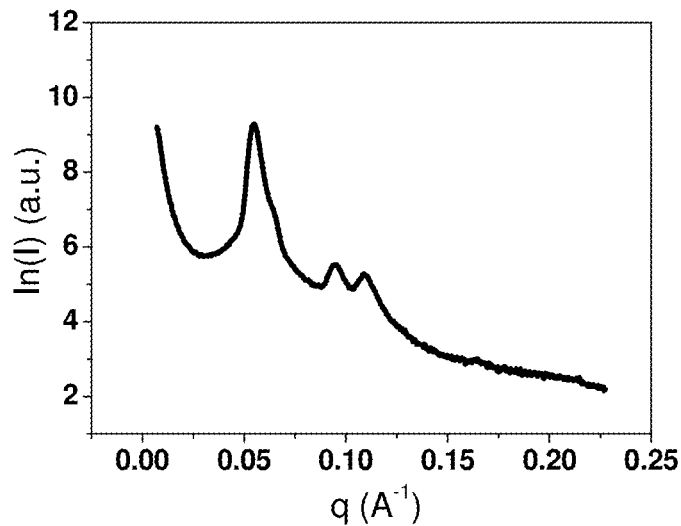
FIG. 25 is a SAXS diagram of the self-assembled product of the Class E block copolymer P2VP-PPFMA-3-67 after thermal quenching at a low temperature (e.g., 160° C.) for a short time (e.g., 60 s).

FIG. 25 is a SAXS diagram of the self-assembled product of the Class E block copolymer P2VP-PPFMA-3-67 after thermal quenching at a low temperature (e.g., 160° C.) for a short time (e.g., 60 s).

It can be seen from FIG. 25 that the block copolymer P2VP-PPFMA-3-67 can be rapid assembled at low temperature to obtain a long-range ordered hexagonal structure, and the assembly-spacing of the block copolymer P2VP-PPFMA-3-67(full-pitch) is 11.4 nm.

Example 15 the Preparation of Class F Block Copolymer P2VP-PPFMA-3-61 ($R_1$=CH$_3$, $R_2$=C$_8$H$_2$F$_{15}$, $R_3$=None)

2.2 ml 2-vinylpyridine and 35 ml THF were treated with triisobutylaluminum solution (M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (1M in hexane) was added and the solution rapidly became orange-red, keeping at −50° C. and reacted for 15 min. The temperature of the dried modified methacrylate monomer F (1.6 ml) was reduced to −30° C., and then the obtained was dropped into the reaction system containing 2-vinylpyridine, keeping at −50° C. and reacted for 30 min. The product was precipitated in ethanol to give 3.0 g of white solid.

The $^1$H-NMR spectrum of the block copolymer P2VP-PPFMA-3-61 is similar to FIG. 23. The GPC analysis shows that the number average molecular weight of the block copolymer P2VP-PPFMA-3-61 is 6900 and PDI thereof is 1.16.

Figure 26:
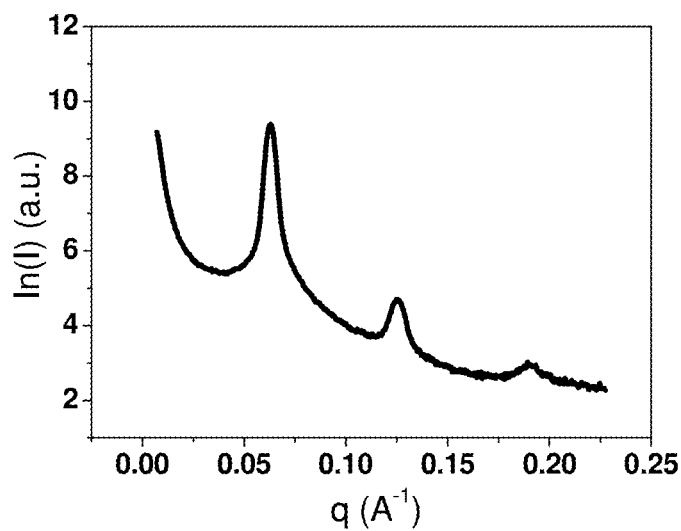
FIG. 26 is a SAXS diagram of the self-assembled product of the Class E block copolymer P2VP-PPFMA-3-61 after thermal quenching at a low temperature (e.g., 160° C.) for a short time (e.g., 60 s).

FIG. 26 is a SAXS diagram of the self-assembled product of the Class E block copolymer P2VP-PPFMA-3-61 after thermal quenching at a low temperature (e.g., 160° C.) for a short time (e.g., 60 s).

It can be seen from FIG. 26 that the block copolymer P2VP-PPFMA-3-61 can be rapid assembled at low temperature to obtain a long-range ordered lamella structure, and the assembly-spacing of the block copolymer P2VP-PPFMA-3-61(full-pitch) is 9.9 nm.

Example 16 the Preparation of Class F Block Copolymer P2VP-PPFMA-3-68 ($R_1$=CH$_3$, $R_2$=C$_8$H$_2$F$_{15}$, $R_3$=None)

1.6 ml 2-vinylpyridine and 35 ml THF were treated with triisobutylaluminum solution (1M in hexane) at 40° C. for 0.5 h, and then transferred to the reaction flask. The reaction flask was returned to room temperature, and stirred to be uniform, and then placed into a cold bath at −50° C. for 15 min. 0.5 ml sec-BuLi (M in hexane) was added and the solution rapidly became orange-red, keeping at −50° C. and reacted for 15 min. The temperature of 1.5 ml of dried modified methacrylate monomer F was reduced to −30° C., and then the obtained was dropped into the reaction system containing 2-vinylpyridine, keeping at −50° C. and reacted for 30 min. The product was precipitated in ethanol to give 2.5 g of white solid.

The 1H-NMR spectrum of the block copolymer P2VP-PPFMA-3-68 is similar to FIG. 23.

The GPC analysis shows that the number average molecular weight of the block copolymer P2VP-PPFMA-3-68 is 5600 and PDI thereof is 1.17.

The self-assemble size of the block copolymer is 9.4 nm according to SAXS results.

Figure 27:
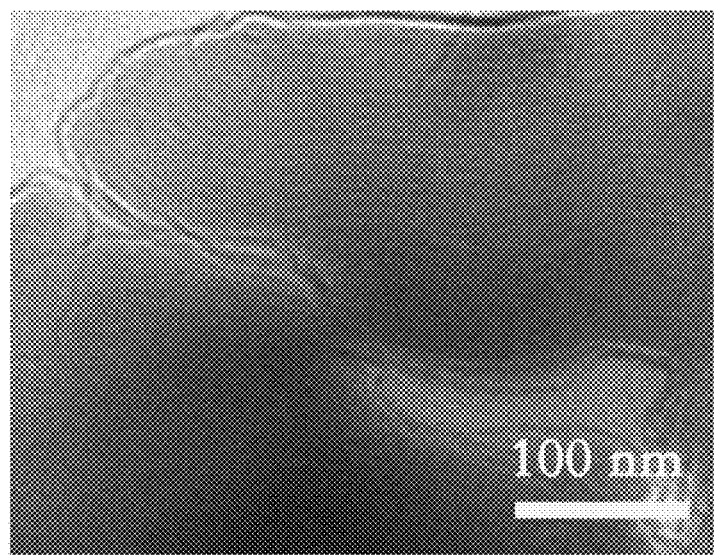
FIG. 27 is a TEM diagram of the self-assembled product of the Class E block copolymer P2VP-PPFMA-3-68 after thermal quenching at a low temperature (e.g., 160° C.) for a short time (e.g., 60 s).

FIG. 27 is a TEM diagram of the self-assembled product of the Class E block copolymer P2VP-PPFMA-3-68 after thermal quenching at a low temperature (e.g., 160° C.) for a short time (e.g., 60 s).

It can be seen from FIG. 27 that the block copolymer P2VP-PPFMA-3-68 can be rapid assembled at low temperature to obtain a long-range ordered lamella structure, and the assembly-spacing of the block copolymer P2VP-PPFMA-3-68(full-pitch) is 7.7 nm.

For convenience, the relevant parameters of the block copolymers in Examples 1-12 are summarized in Table 2 below:

TABLE 2

| Example | Tg | Monomer of block A | Monomer of block B | m:n | PDI | Number average molecular weight (Mn) | Annealing temperature and time for phase separation and self-assembly | Self-assembly spacing (calculated by SAXS)/nm | Self-assembly spacing (calculated by TEM)/nm |
|---|---|---|---|---|---|---|---|---|---|
| 1 | 86° C. | $R_3$=none | $R_1$=CH$_3$, $R_2$=C$_{12}$H$_{10}$F$_{15}$ | 4.3 | 1.13 | 16800 | 80° C. 60s | 14.9 | 13.8 |
| 2 | 75° C. | $R_3$=none | $R_1$=CH$_3$, $R_2$=C$_{12}$H$_{10}$F$_{15}$ | 1.7 | 1.10 | 12500 | 80° C. 60s | 10.3 | 8.6 |
| 3 | 66° C. | $R_3$=none | $R_1$=CH$_3$, $R_2$=C$_{12}$H$_{10}$F$_{15}$ | 0.8 | 1.09 | 11300 | 80° C. 60s | 8.7 | 6.5 |
| 4 | | $R_3$=none | $R_1$=CH$_3$, $R_2$=C$_4$H$_2$F$_7$ | | 1.15 | 12500 | 100° C. 60s | 17.7 | |
| 5 | | $R_3$=none | $R_1$=CH$_3$, $R_2$=C$_4$H$_2$F$_7$ | 3.2 | 1.13 | 16200 | 100° C. 60s | 21.0 | 20.3 |

TABLE 2-continued

| Example | Tg | Monomer of block A (vinyl/R₃ phenyl) | Monomer of block B (R₁, R₂ acrylate) | m:n | PDI | Number average molecular weight (Mn) | Annealing temperature and time for phase separation and self-assembly | Self-assembly spacing (calculated by SAXS)/nm | Self-assembly spacing (calculated by TEM)/nm |
|---|---|---|---|---|---|---|---|---|---|
| 6 | 58° C., 88° C. | $R_3$ =none | $R_1$ =$CH_3$, $R_2$ =$C_4H_2F_7$ | | 1.14 | 19600 | 100° C. 60s | 21.4 | |
| 7 | | $R_3$ =none | $R_1$ =$CH_3$, $R_2$ =$C_{10}H_9F_{12}$ | | 1.17 | 11400 | 80° C. 60s | 16.5 | |
| 8 | 30° C. | $R_3$ =none | $R_1$ =$CH_3$, $R_2$ =$C_{10}H_{21}$ | 2.2 | 1.19 | 18300 | 100° C. 300s | 11.3 | |
| 9 | | $R_3$ =none | $R_1$ =$CH_3$, $R_2$ =$C_{10}H_{21}$ | 1.6 | 1.16 | 14400 | 100° C. 300s | 10.8 | |
| 10 | | R3=none | $R_1$ =$CH_3$, $R_2$ =$C_8H_2F_{15}$ | 2.8 | 1.14 | 5500 | 80° C. 60s | 12.5 | |
| 11 | | R3=none | $R_{21}$ =$CH_3$, $R_2$ =$C_8H_2F_{15}$ | 1.6 | 1.14 | 3900 | 80° C. 60s | 10.4 | |
| 12 | | R3=none | $R_1$ =$CH_3$, $R_2$ =$C_8H_2F_{15}$ | 0.9 | 1.13 | 3500 | 80° C. 60s | 8.8 | |

The relevant parameters of the block copolymers in Examples 13-16 are summarized in Table 3 below:

TABLE 3

| Example | Tg | Monomer of block A (vinylpyridine/R₃) | Monomer of block B (R₁, R₂ acrylate) | m:n | PDI | number average molecular weight (Mn) | Annealing temperature and time for phase separation self-assembly | Self-assembly spacing (calculated by SAXS)/nm | Self-assembly spacing (calculated by TEM)/nm |
|---|---|---|---|---|---|---|---|---|---|
| 13 | | $R_3$ =none | $R_1$ =$CH_3$, $R_2$ =$C_8H_2F_{15}$ | 8.2 | 1.14 | 7800 | 160° C. 60s | 10.9 | |
| 14 | | $R_3$ =none | $R_1$ =$CH_3$, $R_2$ =$C_8H_2F_{15}$ | 2.5 | 1.15 | 8200 | 160° C. 60s | 11.4 | |
| 15 | | $R_3$ =none | $R_1$ =$CH_3$, $R_2$ =$C_8H_2F_{15}$ | 3.7 | 1.16 | 6900 | 160° C. 60s | 9.9 | |
| 16 | | $R_3$ =none | $R_1$ =$CH_3$, $R_2$ =$C_8H_2F_{15}$ | 1.5 | 1.17 | 5600 | 160° C. 60s | 9.4 | 7.7 |

In conclusion, in the block polymer, when the length of carbon chain in block B gradually increases and the monomers in block B have a certain content of fluorine atoms or other heteroatoms, the phase separation size of the block polymer will be decreased. By precise regulation of the number average molecular weight and the proportion of the two blocks of the block polymer, a assembly-spacing of lower than 10 nm (full-pitch) can be obtained, and the half-pitch of 5 nm and below can also be obtained.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed is:

1. A block copolymer, wherein glass transition temperature of the block copolymer is less than 120° C. wherein the block copolymer consists of a block A and a block B, wherein the block A is polymerized from a monomer selected from the group consisting of: vinyl and R3 substituted C6-C10 aryl compounds, and vinyl and R3 substituted C6-C10 heteroaryl compounds containing from 0 to 4 heteroatoms selected from N, O, S or P, wherein, R3 is selected from the group consisting of: none, halogen, substituted or unsubstituted C1-C6 alkyl, and substituted or unsubstituted C1-C6 alkoxy; the block B is polymerized from a monomer represented by

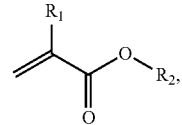

wherein $R_1$ is, substituted or unsubstituted C1-C6 alkyl, $R_2$ is selected from the group consisting of: substituted C1-C30 alkyl, and substituted C3-C30 cycloalkyl; wherein "substituted" means that the group is substituted with one or more substituents selected from halogen; and the number average molecular weight of the block copolymer is from 1000 to 60000.

2. The block copolymer according to claim 1, wherein the molar ratio of the block A and the block B is 1-500:1-500.

3. The block copolymer according to claim 1, wherein $R_2$ is substituted C4-C30 alkyl.

4. The block copolymer according to claim 1, wherein the block A is polymerized from a monomer selected from the group consisting of: styrene, and vinylpyridine; and/or the block B is polymerized from the monomer represented by

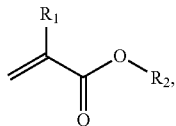

wherein, $R_1$ is C1-C6 alkyl, $R_2$ is fluorine-substituted C1-C30 alkyl, in the fluorine-substituted C1-C30 alkyl, the number of the substituent F is 1 to 60.

5. The block copolymer according to claim 1, wherein the block polymer has one or more characteristics selected from the group consisting of:
  1) polydispersity PDI of the block copolymer is less than or equal to 1.30;
  2) number average molecular weight of the block copolymer is from 1000 to 8000;
  3) annealing temperature for phase separation and self-assembly of the block copolymer is less than or equal to 200° C.;
  4) annealing time for phase separation and self-assembly of the block copolymer is less than or equal to 24 h;
  5) assembly spacing of the product self-assembled by the block copolymer is less than or equal to 50 nm.

6. The preparation method of the block copolymer according to claim 1, wherein the method includes following steps:
  1) providing a homopolymer and a modified monomer, wherein,
     the homopolymer is polymerized from a monomer selected from the group consisting of:
     vinyl and R3 substituted C6-C10 aryl compounds, and vinyl and R3 substituted C6-C10 heteroaryl compounds containing from 0 to 4 heteroatom selected from N, O, S or P, wherein R3 is selected from the group consisting of: none, halogen, substituted or unsubstituted C1-C6 alkyl, and substituted or unsubstituted C1-C6 alkoxy;
     the modified monomer has a formula of

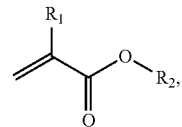

wherein $R_1$ is selected from the group consisting of: H, halogen, substituted or unsubstituted C1-C6 alkyl, substituted or unsubstituted C1-C6 alkoxy, and substituted or unsubstituted C6-C10 aryl, $R_2$ is selected from the group consisting of: substituted C30 alkyl, and substituted C3-C30 cycloalkyl; the "substituted" means that the group is substituted with one or more substituents selected from halogen;
  2) mixing the homopolymer and the modified monomer to obtain the block copolymer.

7. A composite material, wherein, the composite material comprises the block A copolymer according to claim 1.

8. The block copolymer according to claim 1, wherein $R_1$ is unsubstituted C1-C6 alkyl.

* * * * *